United States Patent
Shelchuk et al.

(10) Patent No.: US 7,403,819 B1
(45) Date of Patent: Jul. 22, 2008

(54) PARASYMPATHETIC NERVE STIMULATION FOR CONTROL OF AV CONDUCTION

(75) Inventors: Anne M. Shelchuk, San Rafael, CA (US); Gene A. Bornzin, Simi Valley, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 541 days.

(21) Appl. No.: 10/460,145

(22) Filed: Jun. 11, 2003

Related U.S. Application Data

(60) Provisional application No. 60/389,053, filed on Jun. 12, 2002.

(51) Int. Cl.
*A61N 1/34* (2006.01)
*A61N 1/368* (2006.01)

(52) U.S. Cl. .............................. 607/17; 607/11; 607/12

(58) Field of Classification Search .................... 607/2, 607/9, 14, 19, 20, 25, 11, 12, 17
See application file for complete search history.

(56) References Cited

U.S. PATENT DOCUMENTS

| | | | |
|---|---|---|---|
| 4,712,555 A | 12/1987 | Thornander et al. | 128/419 |
| 4,788,980 A | 12/1988 | Mann et al. | 128/419 |
| 4,940,052 A | 7/1990 | Mann et al. | 128/419 |
| 4,944,298 A | 7/1990 | Sholder | 128/419 |
| 5,024,222 A | 6/1991 | Thacker | 128/419 PG |
| 5,193,535 A | 3/1993 | Bardy et al. | 128/419 D |
| 5,199,428 A * | 4/1993 | Obel et al. | 607/44 |
| 5,203,326 A | 4/1993 | Collins | 128/419 PG |
| 5,237,991 A | 8/1993 | Baker, Jr. et al. | |
| 5,243,980 A | 9/1993 | Mehra | 607/6 |
| 5,330,507 A | 7/1994 | Schwartz | 607/14 |
| 5,330,508 A | 7/1994 | Gunderson | 607/14 |
| 5,334,221 A | 8/1994 | Bardy | 607/14 |
| 5,356,425 A | 10/1994 | Bardy et al. | |
| 5,466,245 A * | 11/1995 | Spinelli et al. | 607/17 |
| 5,466,254 A | 11/1995 | Helland | 607/123 |
| 5,476,483 A | 12/1995 | Bornzin et al. | 607/17 |

(Continued)

FOREIGN PATENT DOCUMENTS

EP 467652 A2 * 1/1992

(Continued)

OTHER PUBLICATIONS

Chen et al., "Intracardiac Stimulation of Human Parasympathetic Nerve Fibers Induces Negative Dromotropic Effects: Implication with the Lesions of Radiofrequency Catheter Ablation," J. Cardiovasc. Electrophysiol., Mar. 1998; vol. 9, No. 3: 245-252.

(Continued)

*Primary Examiner*—Carl Layno
*Assistant Examiner*—Tammie K. Heller

(57) ABSTRACT

Exemplary methods for affecting conduction and/or operation of the AV node and/or AV bundle. Various exemplary methods include delivery of one or more stimulation pulses to affect conduction and/or operation of an AV node and/or AV bundle. Such delivery optionally stimulates nerves and/or tissue. Nerve stimulation optionally includes parasympathetic nerve stimulation to decrease conduction of the AV node and/or AV bundle. Tissue stimulation optionally causes tissue to enter a refractory period. Various exemplary methods include delivering one or more stimulation pulses during postinspiration. Other exemplary methods and/or devices are also disclosed.

6 Claims, 15 Drawing Sheets

U.S. PATENT DOCUMENTS

| | | | |
|---|---|---|---|
| 5,507,784 A | 4/1996 | Hill et al. | 607/14 |
| 5,522,854 A | 6/1996 | Ideker et al. | 607/6 |
| 5,549,655 A * | 8/1996 | Erickson | 607/42 |
| 5,564,422 A | 10/1996 | Chen et al. | |
| 5,578,061 A | 11/1996 | Stroetmann et al. | |
| 5,620,468 A | 4/1997 | Mongeon et al. | |
| 5,690,681 A | 11/1997 | Geddes et al. | |
| 5,700,282 A | 12/1997 | Zabara | 607/6 |
| 5,707,400 A | 1/1998 | Terry, Jr. et al. | |
| 5,720,295 A | 2/1998 | Greenhut et al. | |
| 5,836,974 A | 11/1998 | Christini et al. | 607/5 |
| 5,836,976 A | 11/1998 | Min et al. | 607/6 |
| 6,006,134 A * | 12/1999 | Hill et al. | 607/9 |
| 6,134,470 A | 10/2000 | Hartlaub | 607/14 |
| 6,141,590 A * | 10/2000 | Renirie et al. | 607/20 |
| 6,216,036 B1 | 4/2001 | Jenkins et al. | |
| 6,272,377 B1 | 8/2001 | Sweeney et al. | 600/515 |
| 6,292,697 B1 | 9/2001 | Roberts | |
| 6,314,323 B1 | 11/2001 | Ekwall | 607/23 |
| 6,345,200 B1 | 2/2002 | Mouchawar et al. | |
| 6,449,503 B1 | 9/2002 | Hsu | 600/518 |
| 6,473,644 B1 | 10/2002 | Terry, Jr. et al. | 607/2 |
| 6,611,713 B2 | 8/2003 | Schauerte | 607/14 |
| 6,647,292 B1 | 11/2003 | Bardy et al. | |
| 6,668,191 B1 | 12/2003 | Boveja | |
| 6,687,540 B2 | 2/2004 | Marcovecchio | 607/5 |
| 6,690,971 B2 | 2/2004 | Schauerte et al. | |
| 6,721,597 B1 | 4/2004 | Bardy et al. | |
| 6,754,528 B2 | 6/2004 | Bardy et al. | |
| RE38,654 E * | 11/2004 | Hill et al. | 607/9 |
| 6,859,664 B2 | 2/2005 | Daum et al. | |
| 6,876,880 B2 | 4/2005 | Hess et al. | |
| 6,889,079 B2 | 5/2005 | Bocek et al. | 607/9 |
| 7,146,212 B2 | 12/2006 | Bardy et al. | |
| 2002/0026222 A1* | 2/2002 | Schauerte et al. | 607/14 |
| 2002/0107553 A1 | 8/2002 | Hill et al. | |
| 2003/0040774 A1 | 2/2003 | Terry, Jr. et al. | 607/2 |
| 2003/0078623 A1 | 4/2003 | Weinberg et al. | |
| 2003/0181951 A1 | 9/2003 | Cates | |
| 2004/0230252 A1 | 11/2004 | Kullok et al. | 607/48 |
| 2005/0267542 A1 | 12/2005 | David et al. | 607/17 |

FOREIGN PATENT DOCUMENTS

| | | |
|---|---|---|
| EP | 0 547 734 A2 | 6/1993 |
| EP | 0 547 734 A3 | 6/1993 |
| EP | 0 547 734 B1 | 6/1993 |
| EP | 0688577 A1 | 12/1995 |
| EP | 1 106 206 A2 | 11/2000 |
| EP | 1 304 135 A2 | 4/2003 |
| EP | 1 304 135 A3 | 4/2003 |
| EP | 1106206 A3 | 1/2004 |
| WO | 2002/096512 A1 | 12/2002 |

OTHER PUBLICATIONS

Lazzara et al., "Selective in Situ Parasympathetic Control of the Canine Sinoatrial and Strioventricular Nodes," Circulation Research, Mar. 1973, vol. XXXII:393-401.

Schauerte et al., "Ventricular Rate Control During Atrial Fibrillation by Cardiac Parasympathetic Nerve Stimulation: a Transvenous Approach," J. Am. College of Cardiology, 1999; vol. 34, No. 7:2043-2050.

Waninger et al., "Characterization of Atrioventricular Nodal Response to Electrical Left Vagal Stimulation," Annals of Biomedical Eng, 1999; vol. 27:758-762.

Kulboka et al., "Changes of Heart Electrophysiological Parameters After Destruction of Epicardial Subplexuses that Innervate Sinoatrial Node," Medicina, 2003; 39 Tomas, No. 6: 589-595.

Du et al., "Response to Cardiac Sympathetic Activation in Transgenic Mice Overexpressing $\beta_2$-Adrenergic Receptor," Amer. Phys. Soc., 1996; 0363-6135/96:H630-H636.

Mendelowitz, "Advances in Parasympathetic Control of Heart Rate and Cardiac Function," News Physio. Sci., 1999; 14:155-161.

Mizeres, "The Cardiac Plexus in Man[1]," Amer. J. of Anatomy, 1963; 112:141-151.

Murakami et al., "Effects of Cardiac Sympathetic Nerve Stimulation on the Left Ventricular End-Systolic Pressure-Volume Relationship and Plasma Norepinephrine Dynamics in Dogs," Jpn. Circ. J., 1997; 61:864-871.

Pauza et al., "Morphology, Distribution, and Variability of the Epicardiac Neural Ganglionated Subplexuses in the Human Heart", Anatomical Record, 2000; 259:353-382.

Mazgalev et al., "Autonomic Modification of the Atrioventricular Node During Atrial Fibrillation Role in the Slowing of Ventricular Rate," Circulation, 1999; 99:2806-2814.

Mazgalev et al., "Anatomic-Electrophysiological Correlations Concerning the Pathways for Atrioventricular Conduction," Circulation, 2001; 103:2660-2667.

Paya et al., "Changes in Canine Ventricular Refractoriness Induced by Trains of Subthreshold High-Frequency Stimuli," J. Electrocardiology, 1991; 24(1):63-69.

Wallick et al., "Separate Parasympathetic Control of Heart Rate and Atrioventricular Conduction of Dogs," Am. Phys. Society, 1990; 259(28):H536-H542.

Burger, Andrew J. MD et al., "*Comparison of the Occurrence of Ventricular Arrhythmias in Patients with Acutely Decompensated Congestive Heart Failure Receiving Dobutamine Versus Nesiritide Therapy*," Am J Cardiolol 2001; 88:35-39.

Cao, Ji-Min MD et al., "*Relationship Between Regional Cardiac Hyperinnervation and Ventricular Arrhythmia*," CIRCULATION. 2000;101:1960-1969.

Cohn, Jay N. MD, *Preventing Congestive Heart Failure*, American Family Physician, vol. 57, No. 8 (Apr. 15, 1998), pp. 1901-1904.

Eisenhofer, Graeme PhD et al., "*Cardiac Sympathetic Nerve Function in Congestive Heart Failure*," CIRCULATION. 1996;93:1667-1676.

Frantz, Robert P. MD, "*Beta blockade in patients with congestive heart failure*," Postgraduate Medicine, vol. 108, No. 3 (Sep. 1, 2000), pp. 108-118.

Gomberg-Maitland, Mardi MD et al., "*Treatment of Congestive Heart Failure*," Arch Intern Med. 2001;161:342-352.

Grassi, Guido MD et al., "*Sympathetic Activation and Loss of Reflex Sympathetic Control in Mild Congestive Heart Failure*," CIRCULATION. 1995;92:3206-3211.

Kawada, Toru et al., "*Vagosympathetic interactions in ischemia-induced myocardial norepinephrine and acetylcholine release*," Am J Physiol Heart Circ Physiol. 280:H216-H221, 2001.

Kirchheim, H.R. et al., "Physiology and pathophysiology of baroreceptor function and neuro-hormonal abnormalities in heart failure," Basic Res Cardiol 93;Suppl 1, 1-22 (1998).

Kirchner, A. MD et al., "Left vagus nerve stimulation suppresses experimentally induced pain," NEUROLOGY 2000;55:1167-1171.

Krum, H, "*Sympathetic activation and the role of beta-blockers in chronic heart failure*," Aust NZ J Med 1999; 29:418-427.

Levett, J.M. MD et al. "*Cardiac Augmentation Can Be Maintained by Continuous Exposure of Intrinsic Cardiac Neurons to a $\beta$-Adrenergic Agonist or Angiotensin II*," Journal of Surgical Research 66, 167-173 (1996).

Loh, Evan MD, "*Overview: Old and New Controversies in the Treatment of Advanced Congestive Heart Failure*," Journal of Cardiac Failure, vol. 7, No. 2 Supp. 1 (2001), pp. 1-7.

Mazgalev, Todor N. PhD et al., "*Anatomic Modification of the Atrioventricular Node During Atrial Fibrillation*," CIRCULATION. 1999;99:2806-2814.

Murakawa, Yuji MD et al., "*Effect of Cervical Vagal Nerve Stimulation on Defibrillation Energy—A Possible Adjunct to Efficient Defibrillation*," JPN Heart J 2003;44:91-100.

Olgin, Jeffrey E. MD et al., "*Heterogeneous Atrial Denervation Creates Substrate for Sustained Atrial Fibrillation*," CIRCULATION. 1998;98:2608-2614.

Rahme, Marc M. et al., "*Effect of autonomic neurotransmitters on excitable gap composition in canine atrial flutter*," Can. J. Physiol. Pharmacol. 79:13-17 (2001).

Ringdahl, Erika N. MD, "*Vagally Mediated Atrial Fibrillation in a Young Man*," Arch Fam Med. 2000. 2000; 9:389-390.

Schlepper, M., "*Einflüsse des autonomen Nervensystems bei supraventrikulären Rhythmusstörungen*," Z.Kardiol. 75: Supp. 5, 35-40 (1986).

Shakar, Simon F. MD et al., "*Low-Level Inotropic Stimulation with type III Phosphodiesterase Inhibitors in Patients with Advanced Symptomatic chronic Heart Failure Receiving β-blocking Agents*," Current Cardiology Reports 2001; 3:224-231.

Shamsham, Fadi MD et al. "*Essentials of the Diagnosis of Heart Failure*," Am Fam Physician 2000;61:1319-28.

Sokolovas, V et al., "*Surgical Parasympathetic AV node Denervation in a Canine Model: Anatomical and Electrophysiological Studies*," HEARTWEB, vol. 2, No. 1 (Nov. 1996), pp. 1-8. http://www.heartweb.org/heartweb/1196/ep0007.htm.

Wen, Zu-Chi MD et al., "*Electrophysiological Mechanisms and Determinants of Vagal Maneuvers for Termination of Paroxysmal Supraventricular Tachycardia*," CIIRCULATION. 1998;98:2716-2723.

Bilgutay, Aydin et al., "Vagal tuning; A new concept in the treatment of supraventricular arrhythmias, angina pectoris, and heat failure," J Thorac Cardiovasic Surg Jul. 1968;56(1):71-82.

Wharton, J. Marcos, "Cardiac Potential and Potential Gradient Fields Generated by Single, Combined, and Sequential Shocks During Ventricular Defibrillation," Circulation. 1992;1510-1523.

Zipes, Douglas P. et al, "Termination of Ventricular Fibrillation in Dogs by by Depolarizing a Critical Amount of Myocardium," The American Journal of Cardiology, Jul. 1975;vol. 36:37-44.

NonFinal Office Action, mailed Sep. 26, 2007: Related U.S. Appl. No. 11/058,512.

NonFinal Office Action, mailed Dec. 8, 2005: Related U.S. Appl. No. 10/420,998.

NonFinal Office Action, mailed May 4, 2006: Related U.S. Appl. No. 10/420,998.

NonFinal Office Action, mailed Aug. 17, 2006: Related U.S. Appl. No. 10/846,107.

Notice of Allowance, mailed Feb. 2, 2007: Related U.S. Appl. No. 10/846,107.

NonFinal Office Action, mailed Dec. 5, 2005: Related U.S. Appl. No. 10/460,013.

Final Office Action, mailed Apr. 17, 2006: Related U.S. Appl. No. 10/460,013.

Advisory Action, mailed Jun. 30, 2006: Related U.S. Appl. No. 10/460,013.

NonFinal Office Action, mailed Sep. 14, 2006: Related U.S. Appl. No. 10/460,013.

Notice of Allowance, mailed May 25, 2007: Related U.S. Appl. No. 10/460,013.

NonFinal Office Action, mailed Mar. 3, 2006: Related U.S. Appl. No. 10/460,149.

NonFinal Office Action, mailed Jul. 17, 2006: Related U.S. Appl. No. 10/460,149.

Final Office Action, mailed Dec. 4, 2006: Related U.S. Appl. No. 10/460,149.

Notice of Allowance, mailed Mar. 16, 2007: Related U.S. Appl. No. 10/460,149.

NonFinal Office Action, mailed Feb. 27, 2006: Related U.S. Appl. No. 10/460,597.

Notice of Allowance, mailed Jul. 24, 2006: Related U.S. Appl. No. 10/460,597.

Restriction Requirement, mailed Jan. 5, 2006: Related U.S. Appl. No. 10/702,562.

NonFinal Office Action, mailed Mar. 16, 2006: Related U.S. Appl. No. 10/702,562.

Final Office Action, mailed Aug. 21, 2006: Related U.S. Appl. No. 10/702,562.

Notice of Allowance, mailed Nov. 22, 2006: Related U.S. Appl. No. 10/702,562.

\* cited by examiner

PARASYMPATHETIC NERVE STIMULATION FOR CONTROL OF AV CONDUCTION

PRIORITY CLAIM AND CROSS-REFERENCE TO RELATED APPLICATIONS

The instant application claims priority to U.S. Provisional Applications: 1) Ser. No. 60/389,053, filed Jun. 12, 2002, entitled "Nerve and/or Tissue Stimulation for Control of Conduction and/or Operation of the Atrioventricular Node and/or Atrioventricular Bundle," to Shelchuk, Bornzin and Falkenberg; 2) Ser. No. 60/388,709, filed Jun. 12, 2002; 3) Ser. No. 60/388,784, filed Jun. 12, 2002; 4) Ser. No. 60/388,623, filed Jun. 12, 2002; 5) 60/388,707, filed Jun. 12, 2002; and 6) nonprovisional U.S. application Ser. No. 10/420,998, filed Apr. 21, 2003, entitled "Parasympathetic Nerve Stimulation for ICD and/or ATP Patients," to Shelchuk; all above applications are incorporated by reference herein.

The instant application is related to co-pending U.S. patent application having Ser. No. 10/460,013, filed Jun. 11, 2003, entitled "Vagal Stimulation for Improving Cardiac Function in Heart Failure or CHF Patients," to Shelchuk, which is incorporated by reference herein and which claims priority to a U.S. Provisional Application having Ser. No. 60/388,709, filed Jun. 12, 2002, which is also incorporated by reference herein.

The instant application is related to co-pending U.S. patent application having Ser. No. 10/460,149, filed Jun. 11, 2003, entitled "Parasympathetic Nerve Stimulation for Termination of Supraventricular Arrhythmias," to Shelchuk, which is incorporated by reference herein and which claims priority to a U.S. Provisional Application having Ser. No. 60/388,784, filed Jun. 12, 2002, which is also incorporated by reference herein.

The instant application is related to co-pending U.S. patent application having Ser. No. 10/460,596, filed Jun. 11, 2003, entitled "Arrhythmia Discrimination," to Shelchuk, which is incorporated by reference herein and which claims priority to a U.S. Provisional Application having Ser. No. 60/388,623, filed Jun. 12, 2002, which is also incorporated by reference herein.

TECHNICAL FIELD

Exemplary methods and/or devices presented herein generally relate to cardiac pacing and/or stimulation therapy. Various exemplary methods and/or devices concern stimulating autonomic nerves, other nerves and/or tissue to affect operation and/or conduction of the AV node and/or AV bundle.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atriventricular bundle (AV bundle or His bundle) and then to the ventricles, which causes ventricular contraction. Thus, in a normal heart, ventricular rhythm relies on conduction of action potentials through the AV node and AV bundle.

Regarding the AV node, it is a small subendocardial structure within the interatrial septum, anterior and superior to the coronary sinus. The AV node has extensive autonomic innervation and an abundant blood supply from the large AV nodal artery, which is a branch of the right coronary artery in approximately 90 percent of the population, and from septal branches of the left anterior descending coronary artery (circumflex artery). The AV node forms part of the only "normal" electrical connection between atria and ventricles. While various conduction subpathways may exist in the AV node or AV nodal region, the AV node is known to transmit impulses slowly via at least one pathway, e.g., requiring approximately 60 ms to approximately 130 ms to traverse about 1 cm of node tissue. In general, slowing of an impulse by AV nodal tissue protects the ventricles by typically not allowing all impulses above a certain rate to pass through to the ventricles, which, in turn, prevents the ventricles from racing in response to a rapid atrial rhythm. Under some circumstances, the AV node blocks all impulses to the ventricles. Further, clinical ablation of the AV node can also block all impulses to the ventricles.

En route to the ventricles, action potentials pass via Purkinje fibers, which typically emerge from the distal region of the AV node and converge gradually to form at least part of the AV bundle. Blood supplies the AV bundle from the AV nodal artery and septal branches of the left anterior descending artery. The AV bundle has relatively sparse autonomic innervation and is somewhat encased within a collagenous skeleton. Destruction of the AV bundle, for example, through ablation, may also block all impulses to the ventricles.

While ablation of a patient's AV node and/or AV bundle has been shown to block unwanted conduction of action potentials to the ventricles, these procedures are irreversible; thus, a need exists to slow and/or block action potentials in a reversible manner. As described herein, various exemplary methods and/or exemplary devices stimulate nerves to effectively slow and/or block conduction of action potentials through a patient's AV node and/or AV bundle. Further, various exemplary methods and/or devices accomplish such tasks in a reversible manner.

SUMMARY

Exemplary methods for affecting conduction and/or operation of the AV node and/or AV bundle. Various exemplary methods include delivery of one or more stimulation pulses to affect conduction and/or operation of an AV node and/or AV bundle. Such delivery optionally stimulates nerves and/or tissue. Nerve stimulation optionally includes parasympathetic nerve stimulation to decrease conduction of the AV node and/or AV bundle. Tissue stimulation optionally causes tissue to enter a refractory period. Various exemplary methods include delivering one or more stimulation pulses during postinspiration. Other exemplary methods and/or devices are also disclosed.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
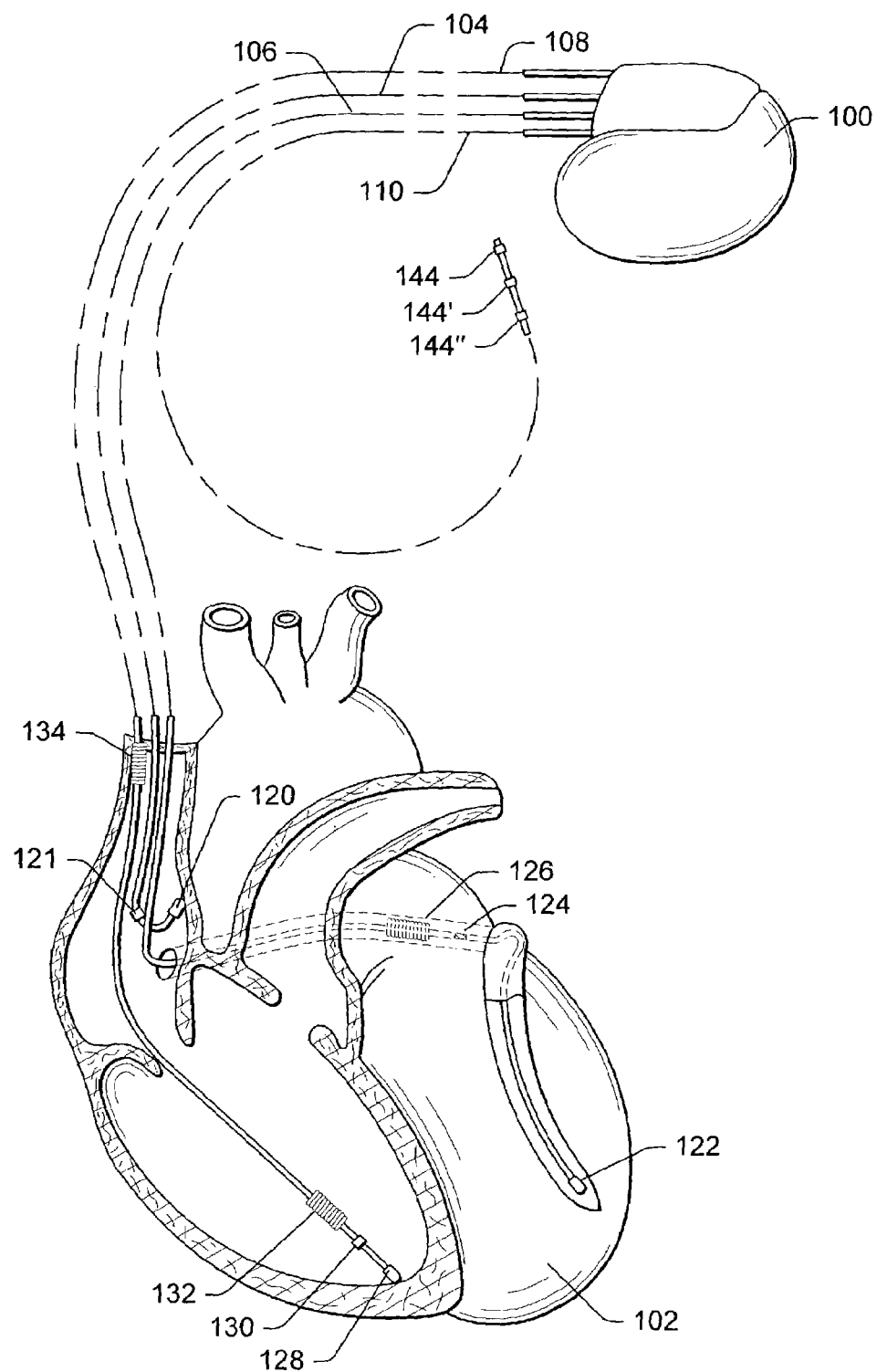
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy.

The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457, 277, filed Dec. 8, 1999, entitled "A Self-Anchoring, Steerable Coronary Sinus Lead" (Pianca et al.); and U.S. Pat. No. 5,466, 254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
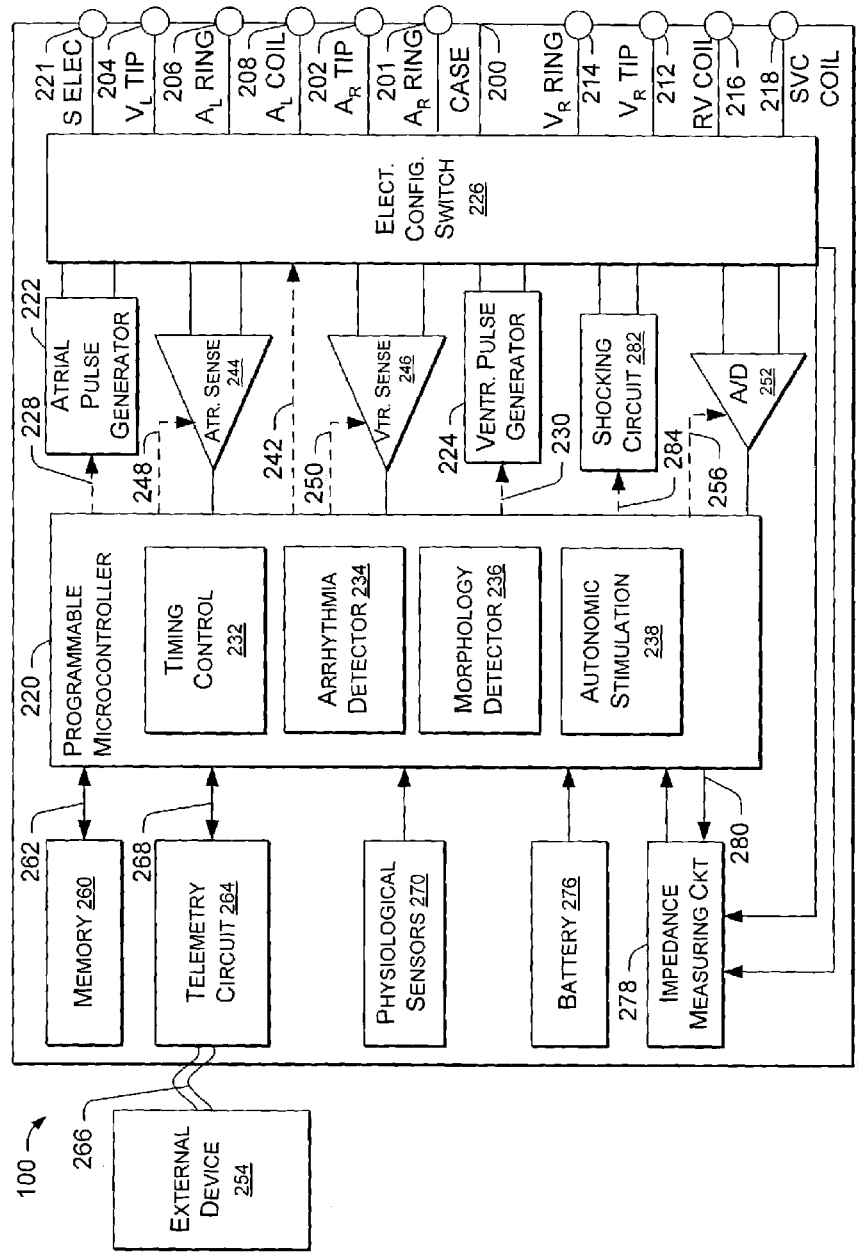
FIG. 2 is a functional block diagram of an exemplary implantable stimulation device illustrating basic elements that are configured to provide cardioversion, defibrillation, pacing stimulation and/or autonomic nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

AV Node and AV Bundle

As already mentioned in the Background section, the AV node and the AV bundle play an important role in the conduction of action potentials to the ventricles. Further, conduction of action potentials may occur via one or more pathways. A recent report by Mazgalev et al., "Anatomic-electrophysiological correlations concerning the pathways for atrioventricular conduction", *Circulation*, 103:2660-2667 (2001), discusses what have traditionally been referred to as "slow" and "fast" conduction pathways.

Figure 3:
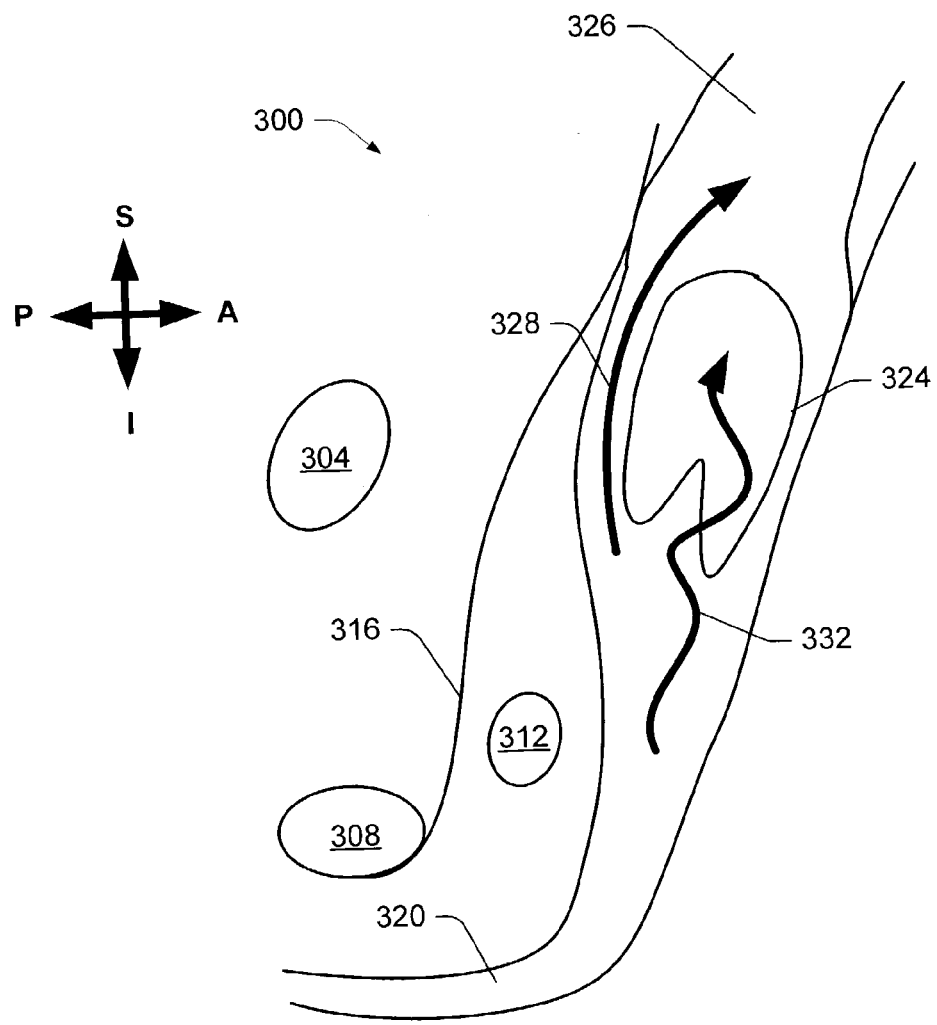
FIG. 3 is an approximate anatomical diagram of an AV nodal region including an AV node and at least part of an AV bundle.

Referring to FIG. 3, an approximate anatomical diagram of the AV nodal region 300 including the AV node and at least part of the AV bundle is shown. As shown, the AV nodal region 300 includes several anatomical landmarks such as the fossa ovalis 304, the inferior vena cava 308, the coronary sinus 312, the tendon of Todaro 316, and the crista terminalis 320. In addition, a directional indicator indicates approximate anatomical directions: "S" superior, "I" inferior, "P" posterior, and "A" anterior. An approximate AV node 324 is also shown, including inferior nodal extensions that lead into a compact cell region, and an AV bundle 326. A "fast" pathway 328 is shown along with a "slow" pathway 332. In FIG. 3, both pathways 328, 332 are oriented primarily from inferior to superior and secondarily from posterior to anterior.

As described by Mazgalev et al., conduction along the slow pathway 332 proceeds from the inferior nodal extensions and through the lower nodal cells, which leads to a superior region of compact cells and on to the AV bundle 326. Mazgalev et al., indicate that the term "slow" seems appropriate because "the pathway [e.g., item 332] encompasses the entire length of the nonpenetrating axis and that the pathway is composed or nodal or nodal-like cells with specific electrophysiological properties that are responsible for a slow velocity of conduction". Mazgalev et al., further note that "the clinical procedure of slow pathway ablation, which is performed in the isthmus between the coronary sinus and the tricuspid valve, may not necessarily eliminate the slow pathway domain" and "may inflict its damage on the plain atrial tissue forming the gap between the inferior nodal approaches and the node itself"; hence, "slow pathway ablation may very well coexist with preservation of the dual-pathway electrophysiology, as has been demonstrated clinically". Therefore, Mazgalev et al., also points to some of the shortcomings associated with "slow pathway ablation".

Regarding the "fast" pathway, Mazgalev et al., state that propagation of an action potential "proceeds toward the most superior extensions of the transitional cells". In FIG. 3, the transitional cells are located within a transitional envelope that extends inferiorly from the inferior nodal extensions and generally surrounds the AV node 324 to even some superior points, e.g., where the tendon 316 joins near the bundle region

326. Such an action potential may form a short transverse route through, for example, a portion of the compact region and into the AV bundle 326. Mazgalev et al., note that while "it may be extremely difficult to ablate the fast pathway selectively . . . lesions on the transitional envelope, especially where it comes in close contact with the compact cells, are likely to produce conduction block".

Mazgalev et al., further note that the slow and fast pathways are not insulated and therefore, "intercommunication between wavefronts can be expected". Consequently, a "fast wavefront running on the surface can exert an electronic depressive effect on the deeper nodal structures" and "ablation of a slow pathway may modulate the refractory properties of the remaining fast wavefront".

In general, AV conduction blocks are categorized as first-degree, second-degree and third-degree. First-degree block is associated with P wave to R wave prolongation (e.g., greater than approximately 0.2 s) with all P waves followed by QRST. Second-degree block is often classified as type I (Wenckebach), type II or high-grade. Type II involves intermittent blocking of P waves with constant P-R intervals. For example, a 2:1 AV block has constant P-R intervals with every second P wave blocked. In high-grade, two or more successive P waves are blocked and, in general, the atrial rate exceeds the ventricular rate. Third-degree block is associated with complete dissociation of P waves and QRST complexes, and, in general, the atrial rate exceeds the ventricular rate.

As described herein, various exemplary methods and/or devices stimulate nerves and/or tissue to cause some degree of irreversible block. Accordingly, stimulation may occur at one or more site proximate to and/or remote from the AV nodal region, including the AV bundle. Various exemplary methods and/or devices stimulate autonomic nerves, other nerves and/or tissue to cause some degree of block.

Nerve/Tissue Stimulation Affects AV Node and/or AV Nodal Region

The tissue of the AV node and/or AV nodal region may be depolarized and/or made to respond more slowly through application of one or more electrical and/or magnetic stimuli. While such a mechanism may stimulate parasympathetic nerves, for example, resulting in the release of acetylcholine, the main thrust of such stimuli is to decrease conduction in the AV node and/or AV nodal region. For example, Paya et al., "Changes in canine ventricular refractoriness induced by trains of subthreshold high-frequency stimuli", *J. Electrocardiology*, 24(1):63-69 (1991), reported that subthreshold conditioning decreased myocardial ventricular excitability, prolonging the effective ventricular refractory period in direct proportion to the subthreshold pulse frequency. Thus, subthreshold stimulation during non-refractory and/or refractory periods of the AV node and/or AV nodal region and/or greater stimulation (e.g., at or above threshold) during a refractory period are optionally used to adjust conduction via the AV node and/or AV nodal region. Of course, stimulation at or above threshold is optionally used during a non-refractory period to cause an evoked response and to affect conduction of the AV node and/or AV nodal region.

In one example, an electrode is positioned proximate to the AV node and used to deliver stimuli to decrease conduction in the AV node and to cause an evoked response of one or more chambers of the heart. Such an electrode may be used in a manner to cause an evoked response when target myocardium is not refractory and to decrease conduction in the AV node when the target myocardium is refractory. Of course, such an electrode may stimulate a parasympathetic nerve that acts to decrease AV nodal conduction as well. Various exemplary methods optionally use such an electrode to achieve a desired AV delay time and/or to stimulate a chamber of the heart.

Parasympathetic Stimulation Affects AV Node and/or AV Nodal Region

Regarding the AV node, a study by Mazgalev et al., "Autonomic modification of the atrioventricular node during atrial fibrillation: role in the slowing of ventricular rate", *Circulation*, 99:2806-2814 (1999), reported that "postganglionic vagal stimulation (PGVS) by short bursts of subthreshold current evokes release of acetylcholine from myocardial nerve terminals" and that "PGVS applied to the atrioventricular node slows nodal conduction". Overall, Mazgalev et al., recognized various attempts at AV node modification (to slow ventricular rate while preserving AV nodal function), noted "inconsistent success rates among investigators", and stated "if this [AV node modification] is unsuccessful, complete AV node destruction can be performed, rendering the patient pacemaker-dependent and undesirably altering the normal sequence of ventricular activation". The goals elaborated by Mazgalev et al., were specifically directed to slowing ventricular rate during atrial fibrillation. As described herein, various exemplary methods and/or devices include parasympathetic nerve, other nerve and/or tissue stimulation to affect the AV node and/or AV nodal region to cause at least some degree of block or decrease in conduction under a variety of conditions, including those unrelated to atrial fibrillation.

A study by Wallick et al., "Separate parasympathetic control of heart rate and atrioventricular conduction of dogs", *Am J. Physiol.*, 259(2 Pt 2):H536-42 (1990), reported that the "inferior vena cava-inferior left atrial fat pad . . . contains nerves that innervate the AV node" and that stimulation of this "fat pad" elicited "a bimodal increase in the atrioventricular conduction time without eliciting any change in the cardiac cycle length". Wallick et al., also noted that they "found an occasional increase in AV conduction time in response to RPV fat pad stimulation", which may be due to "preganglionic fibers that synapse with the parasympathetic ganglia in the IVC-ILA fat pad also pass through or come within close proximity to the RPV fat pad". As described herein, various exemplary methods and/or devices optionally include stimulation of parasympathetic nerves to affect AV node and/or AV nodal regions to cause some degree of block.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrioventricular nodal conduction, and ventricular contractile force, also known as contractility or inotropy. Sympathetic efferent postganglionic neurons, when stimulated, generally increase heart rate and increase contractility. Note that contractility is associated with the term "inotropy", heart rate is associated with the term "chronotropy" and conduction velocity is associated with the term "dromotropy".

As already mentioned, the stimulation of parasympathetic nerves can act to decrease heart rate while stimulation of sympathetic nerves can act to increase heart rate. In addition, as noted by Mendelowitz, "Advances in parasympathetic control of heart rate and cardiac function", *News Physiol. Sci.*, 14:155-161 (1999), "when both parasympathetic and sympathetic activity are present, parasympathetic activity generally dominates" and "increases in parasympathetic activity to the heart evoke a bradycardia that is more pronounced when there is a high level of sympathetic firing". Mendeolowitz also noted that "the release of acetylcholine from parasympathetic neurons might act presynaptically to inhibit the release of norepinephrine from sympathetic nerve terminals".

Regarding sympathetic stimulation, norepinephrine is released by sympathetic nerves. After its release, norepinephrine acts on the sinoatrial node (SA node) to increase the rate of diastolic depolarization, and thereby increase heart rate, and acts on the atrioventricular node (AV node) to increase the velocity of conduction and diminish the refractory period during which the AV node is unresponsive to stimuli coming from the atrium.

Contractility (or inotropy) refers to the force or strength of cardiac muscle contractions. Changes in contractility may be active or passive, for example, stimulation of sympathetic nerves typically causes an active increase in contractility whereas the Frank-Starling mechanism causes a passive increase in contractility. Active contractility involves norepinephrine, which increases myocardial calcium permeability (or conductance) and hence actin/myosin crossbridge interactions. Other mechanisms may also accompany the increase in calcium permeability.

In general, an increase in ventricular contractility (e.g., passive and/or active) causes an increase stroke volume, which, in turn, can increase cardiac output. In particular, an increase in ventricular contractility can cause more complete emptying of the left ventricle. Of course, an increase in filling of the left ventricle (e.g., an increase in end diastolic volume) may also increase stroke volume simply due to the increase in blood volume and/or due to the Frank-Starling mechanism, which causes an increase in passive contractility. An increase in end diastolic volume may be a result of a more relaxed ventricle and/or a result of an increase in fill time (e.g., typically due to an increase in AV delay time). Various exemplary methods described herein aim to increase stroke volume via an increase in AV delay time.

Cardiac output (CO) depends on heart rate (HR) and stroke volume (SV) (e.g., CO equals HR times SV). Changes in ventricular contractility alter the rate of force and pressure development by the ventricle and therefore change the rate of ejection (i.e., ejection velocity). For example, an increase in contractility shifts the Frank-Starling curve, which causes a reduction in end-systolic volume and an increase in stroke volume. The end-systolic pressure-volume relationship (ES-PVR) may define an inotropic state of the ventricle. Treatment of a patient in heart failure with an inotropic drug (e.g., beta-adrenoceptor agonist or digoxin) shifts the depressed Frank-Starling curve up and to the left, thereby increasing stroke volume.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Another term used to describe cardiac operation is "cardiac workload", which is sometimes defined as the product of systolic blood pressure and heart rate. In general, an increase in inotropy, chronotropy and/or dromotropy result in an increase in cardiac workload. Further, sympathetic activity is likely to increase cardiac workload whereas parasympathetic activity is likely to decrease cardiac workload.

Figure 4:
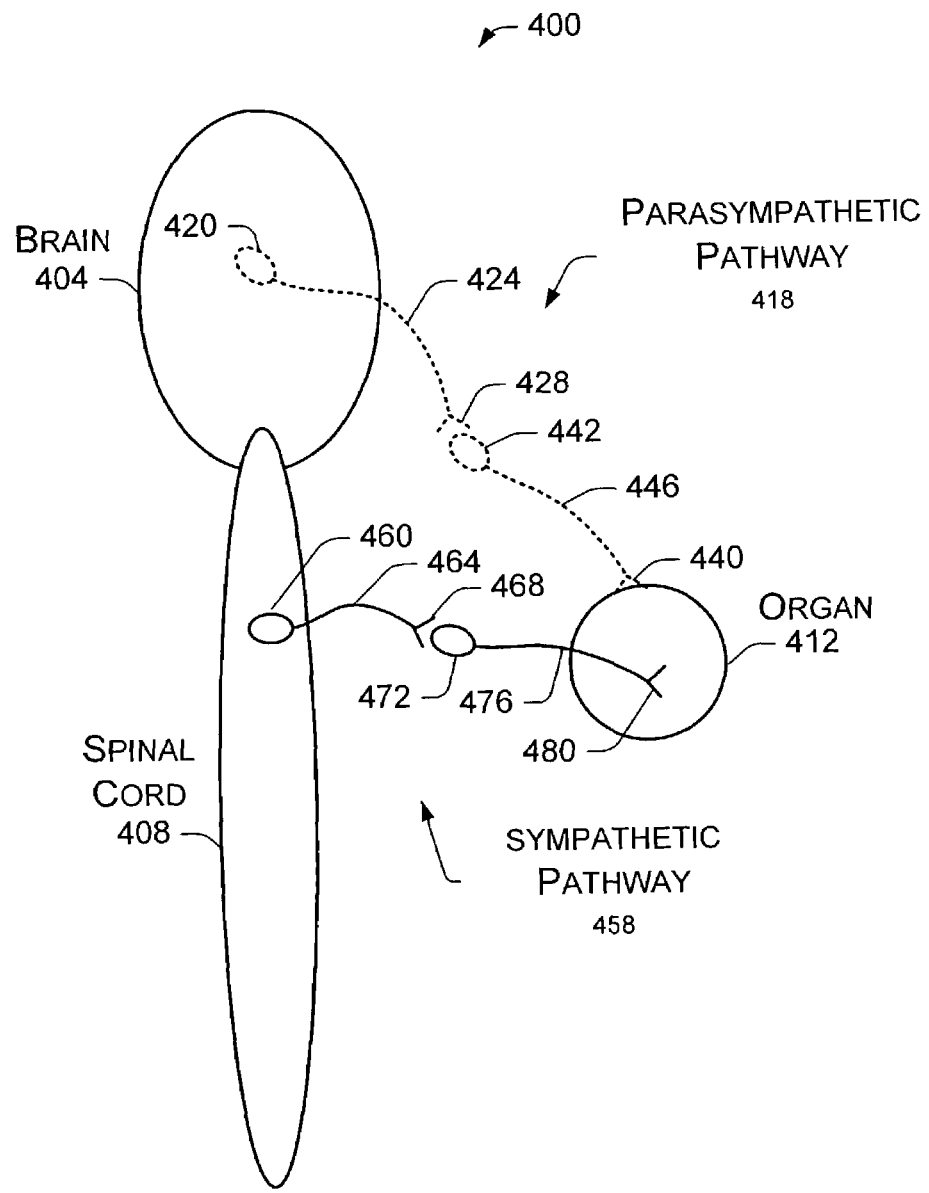
FIG. 4 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 4, a simplified diagram of the autonomic nervous system 400 is shown. The system 400 illustrated includes a brain 404, a spinal cord 408, an organ 412, a parasympathetic efferent pathway 418 and a sympathetic efferent pathway 458. The parasympathetic efferent pathway 418 includes a preganglionic cell body 420 located in the brain 404, a preganglionic axon 424, a synaptic cleft 428, a postganglionic cell body 432, a postganglionic axon 436, and a postganglionic synaptic cleft 440 proximate to the organ 412. An exemplary parasympathetic stimulus originates at the brain 404 and ends at the postganglionic synaptic cleft 440 wherein a chemical is emitted to effect cell of the organ 412. A synaptic cleft may also be referred to as a neuroeffector junction. The sympathetic efferent pathway 458 includes a preganglionic cell body 460 located in the spinal cord 408, a preganglionic axon 464, a synaptic cleft 468, a postganglionic cell body 472, a postganglionic axon 476, and a postganglionic synaptic cleft 480 proximate to the organ 412. An exemplary sympathetic stimulus originates at the spinal cord 408 and ends at the postganglionic synaptic cleft 480 wherein a chemical is emitted to effect cell of the organ 412. In both pathways 418, 458, acetylcholine operates as a neurotransmitter to activate postganglionic neurons, i.e., preganglionic neurons are cholinergic. In parasympathetic pathways (e.g., the parasympathetic pathway 418), postganglionic neurons emit acetylcholine and are therefore cholinergic. However, in many sympathetic pathways (e.g., the sympathetic pathway 458), postganglionic neurons emit norepinephrine and are therefore adrenergic. While FIG. 4 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32. Autonomic pathways than can affect cardiac operation are described in more detail below.

Autonomic Pathways

As already mentioned, the autonomic nervous system includes both sympathetic and parasympathetic nerves. In general, the sympathetic nerves and parasympathetic nerves follow pathways, which, as described in more detail below, are at times to some degree intermingled. Intermingling in the vagosympathetic trunks includes, for example, fibers having a sympathetic core surrounded by a parasympathetic vagal skin. Such "vagosympathetic" fibers may arise from one of the vagosympathetic trunks and descend into epicardial and/or endocardial fibers of the heart. Parasympathetic pathways effecting cardiac operation include the vagus nerve, which is a member of a group of nerves commonly referred to as the cranial nerves. Scientifically, the vagus nerve has been designated as the tenth cranial nerve. There are two of these mixed nerves that act to provide both motor and sensory functions. Each vagus nerve contains both somatic and autonomic branches; however, the autonomic function predominates. Vagus nerves are parasympathetic in nature making up 75% of all parasympathetic fibers passing to the thoracic and abdominal regions of the body. As is the case with most nerves, vagi nerves contain both efferent fibers (e.g., to carry an impulse from its origin in the medulla obligata of the brain to a tissue or an organ), as well as afferent fibers, (e.g., to carry an impulse from a tissue or an organ back to the brain). With vagus nerves, 80% of the fibers are afferent as opposed to efferent. This aids in their active response to the many reflex actions in the body during parasympathetic control. As a whole, the two vagus nerves are very large and work to stimulate a great number of tissues in the body. Vagal stimulation can affect the heart, lungs, esophagus, stomach, small intestine, liver, gall bladder, as well as the upper portions of the ureters.

In general, the right and left vagus nerve pass down the neck as part of right and left vagosympathetic trunks. The right and left vagus also have branches that innervate the heart and lungs. Further down, the left vagus and the right vagus bifurcate into respective left and right ventral and left and right dorsal vagal branches which eventually join. The left and right ventral vagal branches join together to form the ventral vagal trunk on the ventral esophagus while the left and right dorsal vagal branches join together along the dorsal esophagus to form the dorsal vagal trunks. These vagal trunks pass through the esophageal hiatus of the diaphragm and supply the stomach, small intestine, part of the large intestine and major cranial abdominal viscera with parasympathetic innervation. The vagus also includes the right and left recurrent laryngeal nerves, which are somatic, primarily motor subdivisions of the vagus that travel down the neck as part of the right and left vagosympathetic trunks.

Upon stimulation, a vagus nerve releases the hormone acetylcholine at its vagal endings and is, therefore, cholinergic. This is in contrast with adrenergic systems which cause the release of epinephrine and norepinephrine. In general, the release of acetylcholine, rather than the passing of nerve impulses, initiates a specific response at an organ (e.g., the heart, etc.), recognizing that parasympathetic input to the brain is typically associated with a more complex mechanism, which may occur depending on stimulation site and/or stimulation parameters.

Regarding the heart, parasympathetic vagi nerves are distributed to regions of the SA node and the AV node. Release of acetylcholine to these regions typically results in both a decrease in the rate of rhythm of the SA node, as well as a decrease in the cardiac impulse transmission into the ventricles. Consequences of these actions generally include a decrease in heart rate, cardiac output, ventricular contraction, arterial blood pressure, as well as a decrease in overall ventricular pumping.

In general, the right vagus innervates the SA nodal region, the atrial muscle and, to a much lesser degree, the AV nodal region; whereas, the left vagus nerve innervates the SA nodal region and atrial muscle to a lesser degree than it innervates the AV nodal region. Stimulation of the right vagus nerve can predominately slow the SA node rate and thereby reduces heart rate; whereas, stimulation of the left vagus nerve can produce some slowing of the SA node, prolongation of AV conduction and partial or total AV block.

The vagi nerves are also involved in a process known as respiratory sinus arrhythmia (RSA). As stated in Mendelowitz, "Advances in parasympathetic control of heart rate and cardiac function", *News Physiol. Sci.*, 14:155-161 (1999), in RSA, "the heart beats more rapidly in inspiration and slows during postinspiration and expiration". Further, Mendelowitz noted that "cardiac vagal neurons recorded in vivo receive inhibitory synaptic input during inspiration, which is then followed by a rapid depolarization caused by excitatory synaptic input during postinspiration". In general, postinspiration includes expiration.

Figure 5:
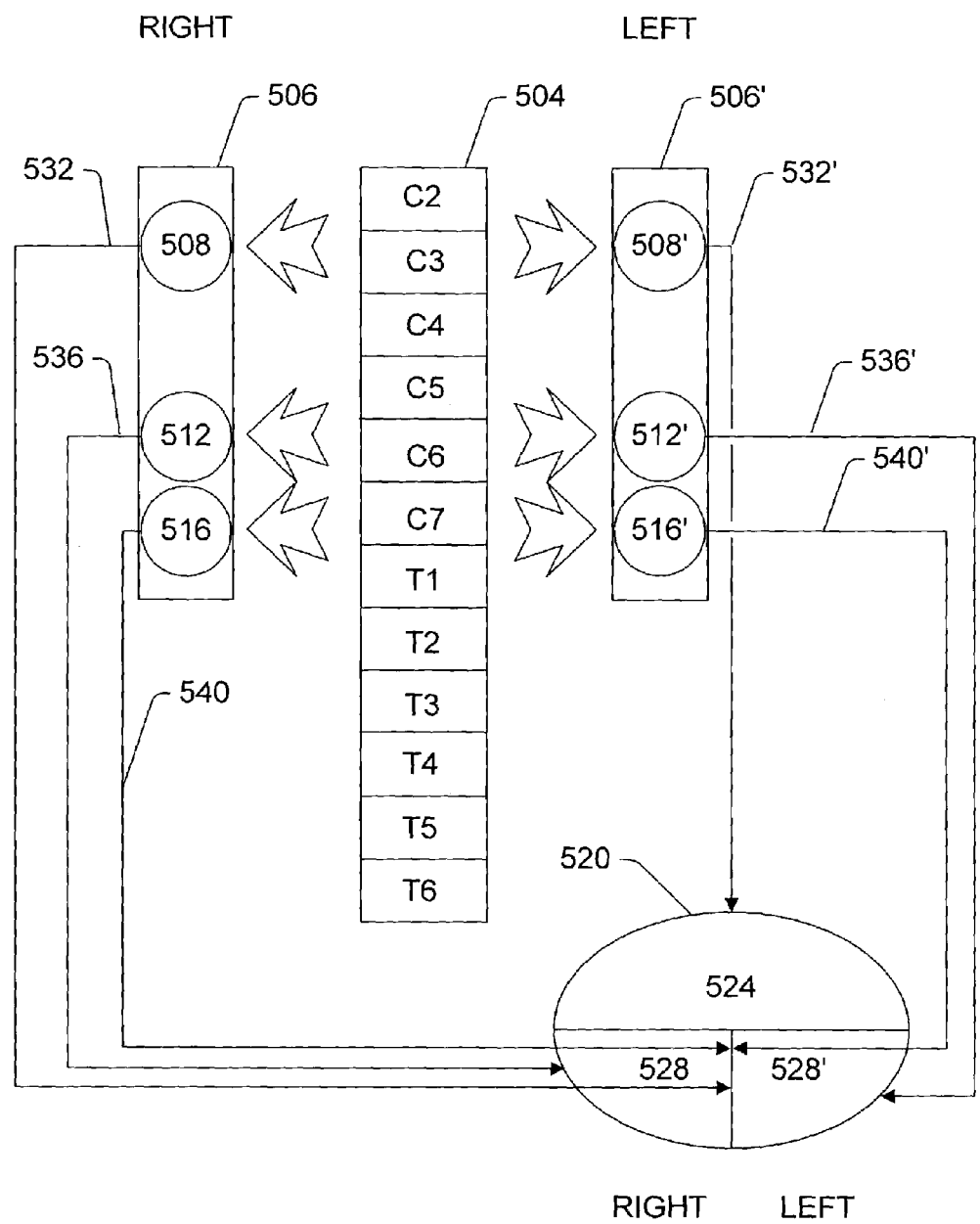
FIG. 5 is a simplified approximate anatomical diagram of sympathetic pathways and/or parasympathetic pathways to the heart.

Referring to FIG. 5, a block diagram of various components of the autonomic nervous system is shown. While FIG. 5 pertains primarily to sympathetic pathways, as already mentioned, intermingling of sympathetic pathways and parasympathetic pathways typically occurs to some degree at various points. The sympathetic nervous system, which is not part of the central nervous system, includes two parallel chains or trunks, a right trunk 506 and a left trunk 506'. Each trunk includes a series of ganglia which lie just lateral to the spinal cord 504 on each side (left and right). In general, the uppermost region of each trunk (506, 406') has three cervical ganglia, which are continuous with the thoracic trunk. The cervical ganglia are known as the right and left superior cervical ganglia (508, 508'), the right and left middle cervical ganglia (512, 512') and the right and left inferior cervical ganglia (516, 516'), the latter of which are known as a stellate ganglion if they combine with a respective first thoracic ganglion. Stellate ganglia exist in approximately 70% to approximately 80% of the population.

Cardiac sympathetic fibers originate in intermediolateral columns of the upper five or six thoracic segments (see T1-T6 in FIG. 5) and lower one or two cervical segments (see C5 and C6 in FIG. 5) of the spinal cord 504. Sympathetic fibers enter the paravertebral chain and typically synapse in the cervical ganglia. Cardiac sympathetic ganglia are generally found close to the spinal column (paravertebral ganglia) and may stem from both thoracic and cervical preganglionic fibers. Postganglionic cardiac sympathetic nerves originate from the left and right ganglia and usually approach the base of the heart (e.g., as superior, middle, and inferior cardiac nerves) along the adventitial surface of the great vessels.

Each of the superior cardiac nerves 532, 532' arises by two or more branches from a respective superior cervical ganglion 508, 508', and occasionally receives a filament from the trunk between a first and/or a second cervical ganglia. The right superior cardiac nerve 532, at the root of the neck, passes either in front of or behind the subclavian artery, and along the innominate artery to the back of the arch of the aorta, where it joins the deep part 528, 528' of the epicardial plexus 520. The right superior cardiac nerve 532 connects with other sympathetic branches. About the middle of the neck the right superior cardiac nerve 532 receives filaments from the external laryngeal nerve; lower down, one or two twigs from the vagus; and as it enters the thorax it is joined by a filament from the recurrent nerve. In addition, filaments from the nerve communicate with the thyroid branches from the right middle cervical ganglion 512. The left superior cardiac nerve 532', in the thorax, runs in front of the left common carotid artery and across the left side of the arch of the aorta, to the superficial part 524 of the epicardial plexus 520.

Each of the middle cardiac nerves 536, 536' (or great cardiac nerves), the largest of the three cardiac nerves, arises from a respective middle cervical ganglion 512, 512', or from a respective trunk 506, 506' between the middle ganglion 512, 512' and the inferior ganglion 516, 516'. On the right side, the right middle cardiac nerve 536 descends behind the common carotid artery, and at the root of the neck runs either in front of or behind the subclavian artery; it then descends on the trachea, receives a few filaments from the recurrent nerve, and joins the right half of the deep part 528 of the epicardial plexus 520. In the neck, it communicates with the right superior cardiac nerve 532 and recurrent nerve. On the left side, the left middle cardiac nerve 536' enters the chest between the left carotid and subclavian arteries, and joins the left half of the deep part 528' of the epicardial plexus 520.

Each inferior cardiac nerve 540, 540' arises from the respective inferior cervical ganglion 516, 516' or the first thoracic ganglion (or stellate ganglion, e.g., 516, 516'). Both right and left inferior cardiac nerves 540, 540' descend behind the subclavian artery and along the front of the trachea, to join the deep part 528, 528' of the epicardial plexus 520. Each of the inferior cardiac nerves 540, 540' communicates freely behind the subclavian artery with the recurrent nerve and the respective middle cardiac nerve 536, 536'.

As already mentioned with reference to FIG. 5, at the base of the heart, the sympathetic fibers form an epicardial plexus 520 that distributes the fibers to the various regions of the heart. The epicardial plexus 520 has a superficial part 524 and a deep part (shown as a right deep part 528 and a left deep part 528' in FIG. 5), see, e.g., Gray's anatomy: the anatomical basis of medicine and surgery, 38th ed. (1995). The deep part 528, 528' lies upon the tracheal bifurcation (at the back of the aorta and in front of the tracheal bifurcation) and consists of cardiac branches from all cervical sympathetic ganglia of both right and left sides except the superior left 508', together with superior and inferior cervical and thoracic cardiac branches of the right vagus nerve (parasympathetic) and superior cervical and thoracic branches of the left vagus nerve (parasympathetic).

Figure 6:
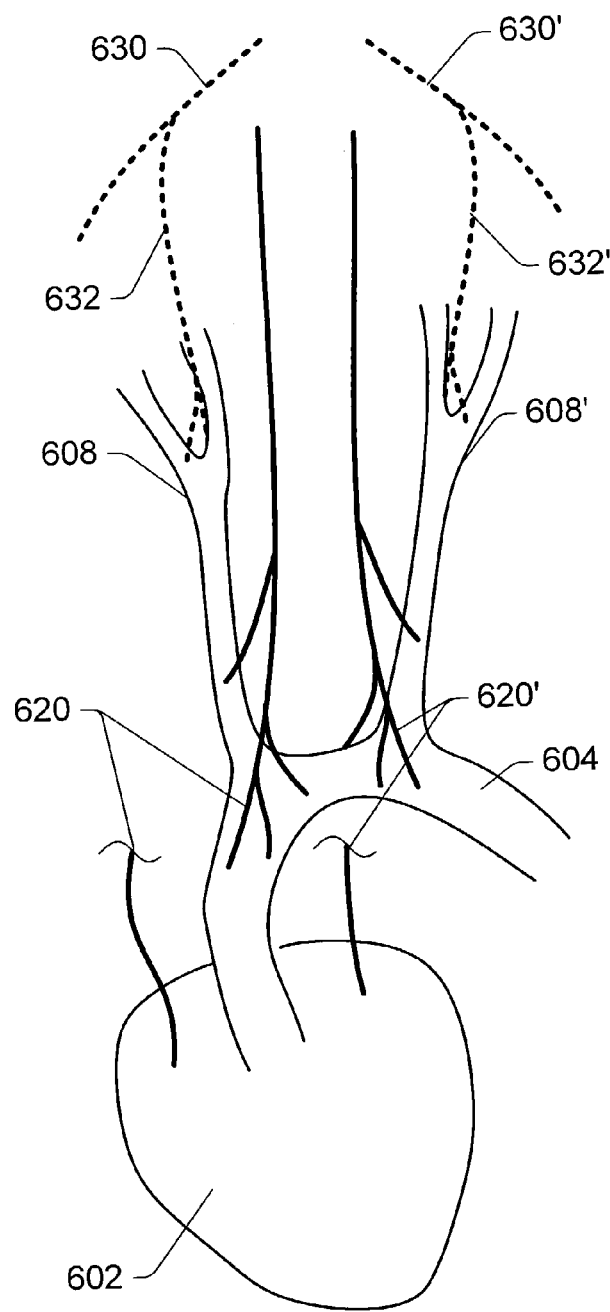
FIG. 6 is a simplified approximate anatomical diagram of parasympathetic afferent pathways.

Referring to FIG. 6, an approximate anatomical diagram of afferent vagal parasympathetic pathways 620, 620' is shown. Vagal afferent pathways include baroreceptors and/or chemoreceptors from the aortic arch 604, carotid arteries 608, 608' and the heart 602. With respect to the heart 602, vagus afferent pathways are known to have receptors associated with atria, ventricles, pulmonary arteries and coronary arteries. Also shown in FIG. 6 are the glossopharyngeal nerves 630, 630' and sinus branches thereof 632, 632'. In general, such afferent pathways lead to the nucleus tractus solitarius in the brainstem. In addition, stimulation of such afferent pathways typically leads to a depressor response. However, a controversial and seemingly undocumented (in humans) reflex known as the "Bainbridge reflex" can increase heart rate due to an increase of the right atrial pressure. In general, cardiac receptors that lead to a neural response are classified as "A" or "B" receptors. B receptors are the predominant stretch receptors and are stimulated by passive stretch of the atria usually during later diastole. B receptors, when stimulated, cause a response similar to baroreceptors, e.g., inhibition of sympathetic nerves and/or excitation of parasympathetic nerves.

Another group of receptors known as left atrial volume receptors respond to increases in transmural pressure: e.g. from increased left atrial volume. Impulses transmitted to the osmoregulatory centers of the hypothalamus result in reduced ADH (antidiuretic hormone, vasopressin) secretion thereby increasing body water loss. Reflex hypotension and bradycardia sometimes follow left atrial distention. With hemorrhage and decreases in left atrial pressure, ADH secretion is increased to induce water retention. Receptors can also cause hormone secretion. For example, mammalian atria have secretory granules containing a small peptide, atrial natriuretic peptide (ANP). ANP is secreted on stretch of the atria. This potent, short lived peptide induces renal secretion of sodium and increase diuresis thus serving to decrease volume. ANP appears to act to decrease CO by decreasing systemic resistance and by increase capillary filtration.

Ventricular, mostly left ventricle, responses include the Bezold-Jarish Reflex, which results from ventricular wall distention stimulating ventricular mechanoreceptors. Such receptors appear to be active only with extreme conditions to protect the ventricle from volume overload (elicit hypotension and bradycardia). The response is a reflex vagal slowing of the heart and simultaneous inhibition of sympathoadrenal activity. The reflex protects against cardiac overstrain, pulmonary edema, and hypovolemia whenever cardiac distention is excessive (e.g., in some CHF patients). The reflex, transmitted by afferent vagal fibers, is thought to exert its sympathetic block via release of endogenous opioids likely acting on the delta-type opioid receptors in the brain.

Epicardial Autonomic Pathways

Pauza et al., "Morphology, distribution, and variability of the epicardiac neural ganglionated subplexuses in the human heart", *The Anatomical Record* 259(4): 353-382 (2000), reported that the epicardial plexus forms seven subplexuses: (I) left coronary, (II) right coronary, (I11) ventral right atrial, (IV) ventral left atrial, (V) left dorsal, (VI) middle dorsal, and (VII) dorsal right atrial. Pauza et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza et al., also note that diagrams from Mizeres, "The cardiac plexus in man", *Am. J. Anat.* 112:141-151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". Further, Pauza et al., also state that the left coronary (I), right coronary (II), ventral left atrial (IV) and middle dorsal (VI) subplexuses "may be considered as being formed by the deep extrinsic plexus that receives equally from both vagi and sympathetic trunks". Note that in the Pauza et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3 and FIG. 4. Thus, the term "postganglionic neurons" includes epicardiac/epicardial preganglionic neurons as well as epicardiac/epicardial postganglionic neurons.

Neuroeffectors

Upon stimulation, end terminals (or terminal knobs) of the postganglionic sympathetic nerves (e.g., epicardial postganglionic sympathetic nerves) release norepinephrine, which acts upon the myocardium. Following stimulation and release, norepinephrine remains active for several seconds; norepinephrine may then be reabsorbed by the terminal, diffuse out of the area, or be inactivated by enzymes. The adrenal medulla also secretes norepinephrine (e.g., 75 percent epinephrine and 25 percent norepinephrine) and produces a peripheral effect that typically lasts much longer than that produced by stimulation of the sympathetic postganglionic terminal knobs. While circulating norepinephrine can increase contractility, the effect on normally innervated hearts is relatively minor with respect to norepinephrine released by end terminals. Heart rate, although initially stimulated by norepinephrine, usually decreases over time due to activation of baroreceptors and vagal-mediated (parasympathetic) slowing of the heart rate.

Cardiac tissue membrane receptors, such as alpha receptors and beta receptors, receive chemicals emitted by postganglionic nerves. Alpha receptors are the most common type of sympathetic receptor and they respond strongly to norepinephrine and weakly to epinephrine. Beta receptors are also adrenergic and include beta-1, beta-2 and beta-3 receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. In contrast, parasympathetic cholinergic muscarinic receptors act on the sinoatrial (SA) node to decrease heart rate and act on the atrioventricular (AV) node to decrease conduction velocity. Adrenergic antagonists (indirect action) include beta-blockers such as proranolol and alpha-blockers such as phentolamine that inhibit receptors. Cholinergic antagonists (indirect action) include alpha-blockers such as atropine.

Electrical and/or Magnetic Stimulation of Autonomic Nerves

Electrical stimulation of autonomic nerves has been reported in the literature, see, e.g., Murakami et al., "Effects of cardiac sympathetic nerve stimulation on the left ventricular end-systolic pressure-volume relationship and plasma norepinephrine dynamics in dogs", *Jpn. Circ. J.* 61(10): 864-71 (1997); and Du et al., "Response to cardiac sympathetic activation in transgenic mice overexpressing beta 2-adrenergic receptor". *Am-J-Physiol.* Aug; 271(2 Pt 2): H630-6 (1996). Magnetic stimulation of nerves has also been reported, for example, where a nerve is exposed to a time-varying magnetic field, which may induce electrical currents in the nerve.

According to various exemplary methods and/or devices described herein, a series of pulses, or a pulse train, is typically delivered by an implantable stimulation device to stimulate an autonomic nerve, other nerve and/or tissue. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency for nerve and/or tissue stimulation include frequencies ranging from approximately 0.1 to approximately 100 Hz, and, in particular, frequencies ranging from approximately 1 Hz to approximately 20 Hz. Of course, higher frequencies higher than 100 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 2 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 1 V to approximately 20 V.

For pulses delivered by implantable stimulation devices having a fixed or otherwise limited power supply, i.e., a power supply having power limitations, average power of a pulse or a pulse train is usually limited acutely by the power capability of the power supply (e.g., battery, fuel cell, nuclear generator, etc.) and chronically by the capacity of the power supply and desired longevity of the device's usefulness. Average power of a pulse is generally given as peak power averaged over one cycle. For example, given a voltage of 10 V, a resistance of 1000 ohms, a pulse frequency of 20 Hz and a pulse width of 1 ms, the peak power is given as voltage squared divided by resistance, which is 0.1 W, and the average power is 20 Hz multiplied by 1 ms multiplied by 0.1 W, which is 0.002 W or 2 mW. The term "power", as used herein, includes, but is not limited to, peak power and average power.

Current drain is another factor often considered when determining power limitations of a power supply. Current drain is generally defined as the average amount of current drawn from a power supply in an implantable pulse generator in one hour. Current drain depends on many factors, including how frequently the device delivers pulses and at what parameters, the circuitry and/or the type of stimulation lead. Current drain is commonly expressed in millionths of an ampere or microamperes. A power drain based on current drain may be determined by the product of current drain and voltage. Such a power is optionally useful in determining a maximum power level for an autonomic stimulation pulse or pulses. Of course, such a power is optionally useful in determining a maximum power level for any stimulation pulse or pulses In general, a maximum power level or maximum power demand for an implantable device may be determined, in part, by the product of the voltage times the current capability of the battery (or other power supply) less circuit inefficiencies. Of course, desired power supply life (e.g., battery life) and/or other factors may be considered. For example, some implantable stimulation devices have a continuous power drain for one function (e.g., to drive a microchip, microprocessor or timing circuitry) and an intermittent function (e.g., such as pacing, measuring, signaling, etc.) which has intermittent power utilization. Consideration of such factors may be necessary in determining a tolerable and/or maximum power level and, in particular, in determining pulse parameters.

Vessels and Stimulation of Autonomic Nerves, Other Nerves and/or Tissue

According to various exemplary methods and stimulation devices described herein, and equivalents thereof, stimulation of parasympathetic nerves, other nerves and/or tissue allows for influence of cardiac activity. For example, various exemplary methods and corresponding stimulation devices rely on placement of one or more electrodes in a vessel, e.g., an epicardial vein or an epicardial venous structure. Suitable epicardial veins or venous structures include the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium.

Other exemplary methods and/or devices rely on placement of one or more electrodes in a non-epicardial vein. Such exemplary methods and/or devices are optionally suitable for stimulation of parasympathetic nerves at locations, for example, generally along a parasympathetic pathway between the heart and brain. Further, other exemplary methods and/or devices rely on placing one or more electrodes through the wall of a vein and proximate to a parasympathetic nerve, other nerve and/or tissue.

Figure 7:
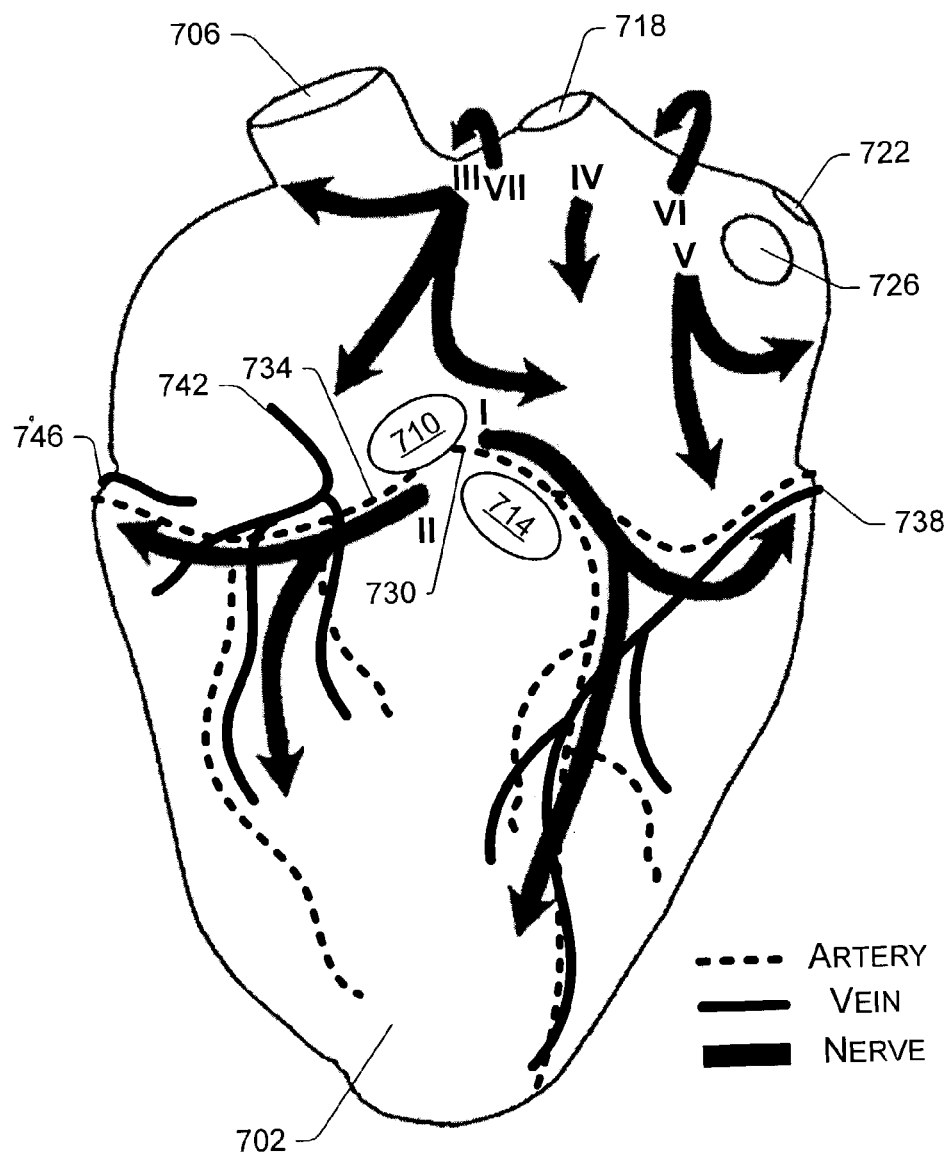
FIG. 7 is an approximate anatomical ventral view diagram of a human heart including some arteries, veins and nerves.

Referring to FIG. 7, a ventral diagram of a human heart 702 is shown. Various anatomical features of the heart 702 are also shown and include an opening to the superior vena cava 706, an opening to the aorta 710, an opening to the pulmonary trunk 714, an opening to the right superior pulmonary vein 718, an opening to the left inferior pulmonary vein 722, and an opening to the left superior pulmonary vein 726. FIG. 7 also shows some of the epicardial arteries (thick dashed lines) and veins (thick solid lines). Under normal conditions, epicardial arteries carry oxygenated blood to the myocardium, primarily myocardium of the ventricles while epicardial veins carry blood deoxygenated by the myocardium to the right atrium of heart 702. Pressure in the veins is generally, on average, much less than pressure in the arteries.

Two major epicardial arterial networks are shown in FIG. 7 and associated with the left coronary artery 730 and the right coronary artery 734. The left coronary artery 730 stems from the aorta near the opening to the aorta 710 and travels along the base of the left ventricle where it branches. One branch of the left coronary artery travels on the epicardial surface of the left ventricle toward the apex of the heart 702 (known as the left anterior descending artery) while another branch travels on the epicardial surface of the left ventricle toward the dorsal side of the heart 702 (known as the circumflex branch of the left coronary artery). The right coronary artery 734 stems from the aorta near the opening to the aorta 710 and travels along the base of the right ventricle where it branches. Various branches of the right coronary artery 734 travel on the epicardial surface of the right ventricle while at least one branch travels on the epicardial surface of the right ventricle toward the dorsal side of the heart 702.

Three major epicardial venous networks are shown in FIG. 7, which are associated with the great cardiac vein 738, the anterior cardiac vein 742, and the small cardiac vein 746. The great cardiac vein 738 receives blood from a network that spreads across the ventral side of the epicardial surface of the left ventricle and major branches of the network extend toward the apex of the heart 702. As already mentioned, the great cardiac vein 738 travels on the epicardial surface near the base of the left ventricle to the dorsal side of the heart 702 where it joins the coronary sinus vein. The anterior cardiac vein 742 receives blood from a network that spreads across the ventral and dorsal sides of the epicardial surface of the right ventricle and major branches of the network extend toward the apex of the heart 702. As already mentioned, the anterior cardiac vein empties into the right atrium of the heart 702. The small cardiac vein 746 travels from the ventral epicardial surface to the dorsal epicardial surface where it empties into the coronary sinus.

FIG. 7 also shows the seven subplexuses as identified by Pauza et al. Preganglionate nerves enter the left coronary subplexus (I) and the right coronary subplexus (II) approximately between the opening to the aorta 710 and the opening to the pulmonary trunk 714. Preganglionate nerves enter the ventral right atrial subplexus (III) at the superior interatrial sulcus and non-regularly on the ventral surface of the root of the superior vena cava while preganglionated nerves enter the ventral left atrial subplexus (IV) approximately between the superior interatrial sulcus and left atrial nerve fold. Preganglionated nerves enter the left dorsal subplexus (V) approximately at the left atrial nerve fold and preganglionated nerves enter the middle dorsal subplexus (VI) approximately between the right and left superior pulmonary veins (see, e.g., 718, 726) and, non-regularly, between the right pulmonary veins and the inferior vena cava. Preganglionated nerves enter the dorsal right atrial subplexus (VII) approximately between the superior vena cava and the right superior pulmonary vein (see, e.g., 706, 718). As already mentioned, postganglionated nerves, and some preganglionated nerves, spread out from the subplexuses (I-VII) across the epicardial surface of the heart 702. The spreading of such nerves is shown by the thick solid arrows in FIG. 7 and FIG. 8, the latter of which shows a dorsal diagram of the heart 702.

Figure 8:
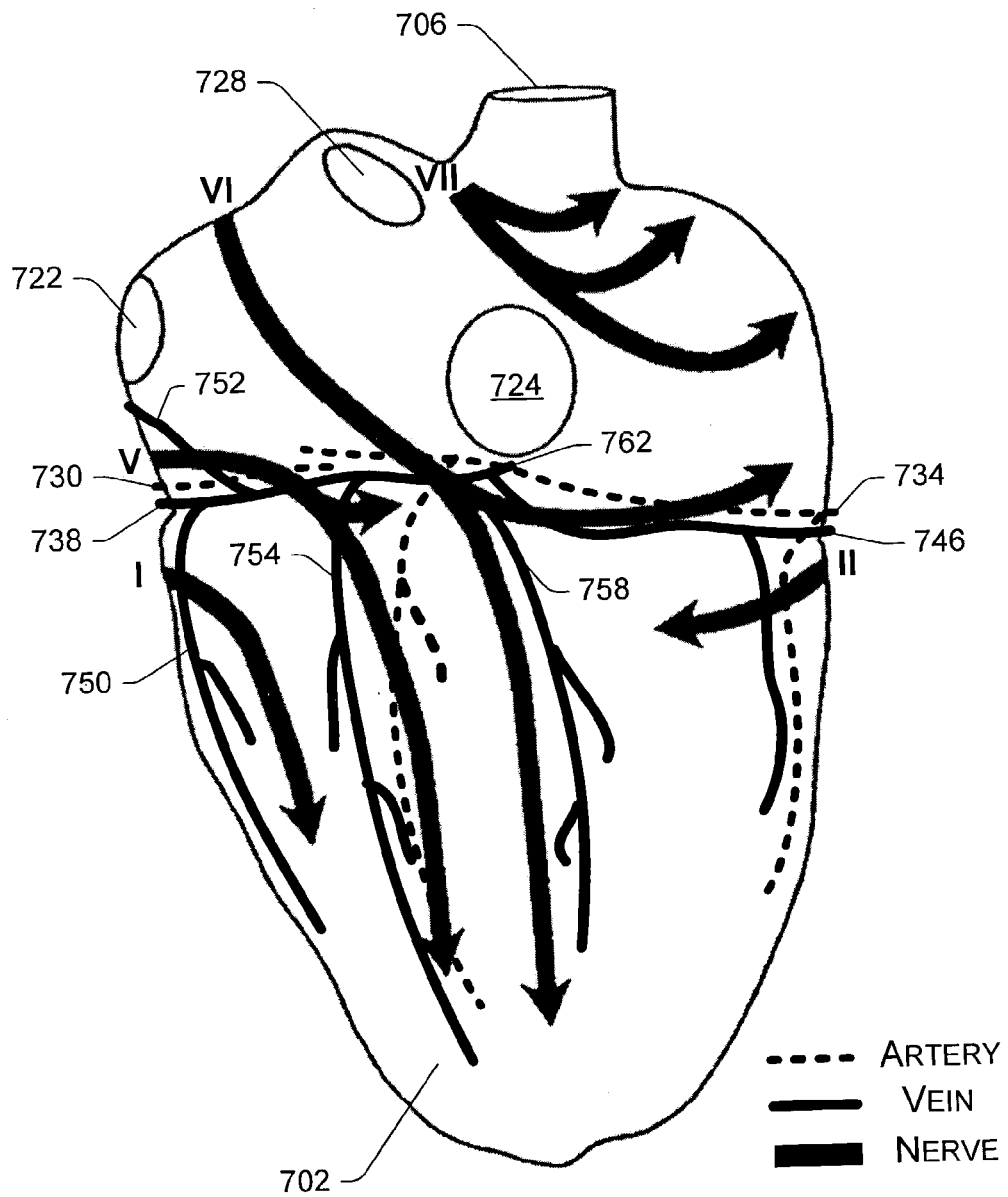
FIG. 8 is an approximate anatomical dorsal view diagram of a human heart including some arteries, veins and nerves.

Referring to FIG. 8, a dorsal diagram of the human heart 702 is shown. Various anatomical features of the heart 702 are also shown and include an opening to the superior vena cava 706, an opening to the inferior vena cava 724, an opening to the right inferior pulmonary vein 728, and an opening to the left inferior pulmonary vein 722. FIG. 8 also shows some of the epicardial arteries (thick dashed lines) and veins (thick solid lines). The arterial and venous networks shown on the dorsal epicardial surface of the heart 702 include extensions of networks from the ventral epicardial surface. For example, the dorsal epicardial surface includes networks stemming the right coronary artery 734 and the left coronary artery 730. In particular, the circumflex branch of the left coronary artery 730 is shown along with various extensions of the right coronary artery 734 one of which approaches the end of the circumflex branch. Venous epicardial structures shown in FIG. 8 include the coronary sinus 762, the great cardiac vein 738, the small cardiac vein 746, the oblique vein of the left atrium 752, the left marginal vein 750, the posterior vein of the left ventricle 754, and the middle cardiac vein 758. The aforementioned veins (738, 746, 750, 752, 754, 758) empty into the coronary sinus 762.

FIG. 7 also shows, via thick solid arrows, neural extensions of five of the subplexuses as identified by Pauza et al. Neural extensions of the left coronary subplexus (I) descend toward the apex of the heart 702 at and/or near the left marginal vein 750 and the posterior vein of the left ventricle 754. Neural extensions of the right coronary subplexus (II) traverse the heart 702 at and/or near the right coronary sulcus. Neural extensions of the left dorsal subplexus (V) descend toward the apex of the heart 702 at and/or near the posterior vein of the left ventricle 754 while neural extensions of the middle dorsal subplexus (VI) descend towards the apex of the heart 702 at and/or near the middle cardiac vein 758 and the small cardiac vein 746. Neural extensions of the dorsal right atrial subplexus (VII) extend around the right atrium at and/or near the superior vena cava (see, e.g., 706) and the inferior vena cava (see, e.g., 724).

As shown in FIGS. 7 and 8, various epicardial veins or venous structures travel at and/or near epicardial subplexuses and/or epicardial extensions of epicardial subplexuses. According to various exemplary methods and/or stimulation devices described herein, at least one electrode is placed in the lumen of an epicardial vein or venous structure and/or through the wall of an epicardial vein or venous structure. Further, upon passing current through the at least one electrode, neural and/or tissue stimulation occurs, which may cause release of a neuroeffector, such as, but not limited to, acetylcholine.

Stimulation of Nerves and/or Tissue

Figure 9:
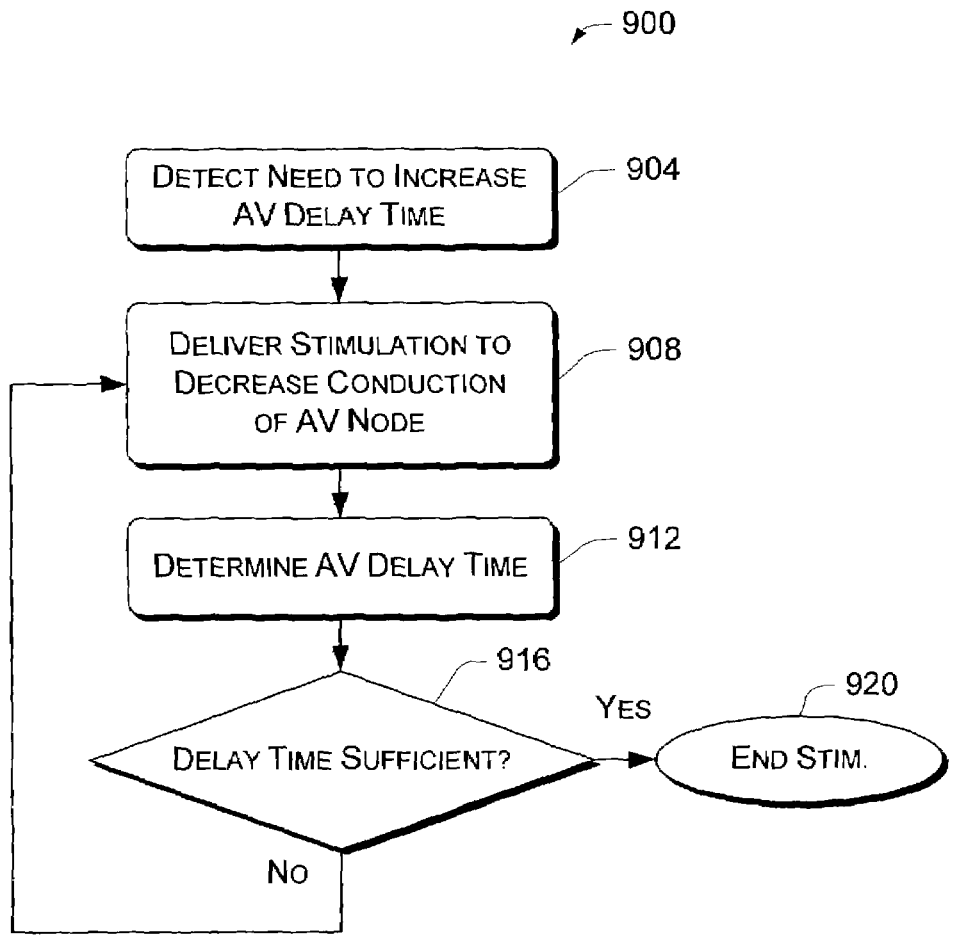
FIG. 9 is a block diagram of an exemplary method for stimulating a parasympathetic nerve to affect conduction of a patient's AV node.

FIG. 9 shows a block diagram of an exemplary method 900 that includes stimulation to decrease AV nodal conduction. In this example, the term AV node may include AV bundle. In a detection block 904, a need to increase AV delay time is detected. The need may be based on physiologic and/or other factors. For example, an implanted device, a patient and/or a physician may aid in detecting a need to increase AV delay time. An implanted device may rely on one or more sensors and/or an algorithm to detect a need to increase AV delay time, a patient may experience symptoms associated with inadequate cardiac function that may benefit from an increase in AV delay time, and/or a physician may wish to make a diagnosis or to prescribe a therapy that relies on a certain minimum AV delay time.

A stimulation delivery block 908 follows, wherein stimulation is delivered to decrease conduction of the AV node. In the exemplary method 900, the stimulation may be directed to a parasympathetic nerve, another nerve and/or tissue. For example, stimulation of a parasympathetic nerve may cause a decrease in AV conduction as described above while stimulation of another nerve or tissue may cause the AV node to experience at least some refractoriness. A determination block 912, which may occur during or after delivery of the stimulation, aims to determine the effect of the stimulation on AV delay time. Such a determination block may compensate for respiratory effects on AV delay time, for example, AV delay time may be measured over a number of cardiac cycles wherein the number covers both inspiration and expiration phases of a respiratory cycle (e.g., one, two, three or more respiratory cycles). The determination block 912 may determine an average or other statistical delay time. In general, the determination block 912 relies on detection of an atrial event and detection of a ventricular event; however, other techniques may be available to determine AV delay time.

According to the exemplary method 900, responsive to the determining, a decision block 918 decides whether the AV delay time is sufficient, for example, with respect to a desired increase and/or some minimum AV delay time. If the decision block 918 decides that the delay time is sufficient, then the method 900 continues in an end block 920, which halts or ramps down the stimulation of the delivery block 908. If the decision block 916 decides that the delay time is not sufficient, then the method 900 continues at the delivery block 908. Delivery of stimulation via the delivery block 908 may be continuous or periodic, for a set period of time and/or a number of cardiac events. Various exemplary methods of stimulating are described further below and may be implemented in the exemplary method 900. Continuation at the delivery block 908 optionally includes adjusting one or more parameters related to the stimulation, wherein the adjusting optionally relies on the determination of the determination block 912 and/or other factors (e.g., whether the need to increase AV delay time still exists).

The exemplary method 900 may be implemented to increase end diastolic volume, for example, via an increase in AV delay time that results in an increase in ventricular fill time. The exemplary method 900 may optionally include a ventricular stimulation block that delivers a ventricular stimulus if the determination block 912 determines that AV delay time is too long or that some significant degree of AV block has occurred (e.g., 2°, 3°, etc.). Such a ventricular stimulation block may continue until the AV delay time shortens or the AV block dissipates, if possible.

The exemplary method 900 may be implemented in conjunction with one or more pacing therapies, wherein an implantable stimulation device delivers pacing stimuli to one or more chambers of the heart.

Figure 10:
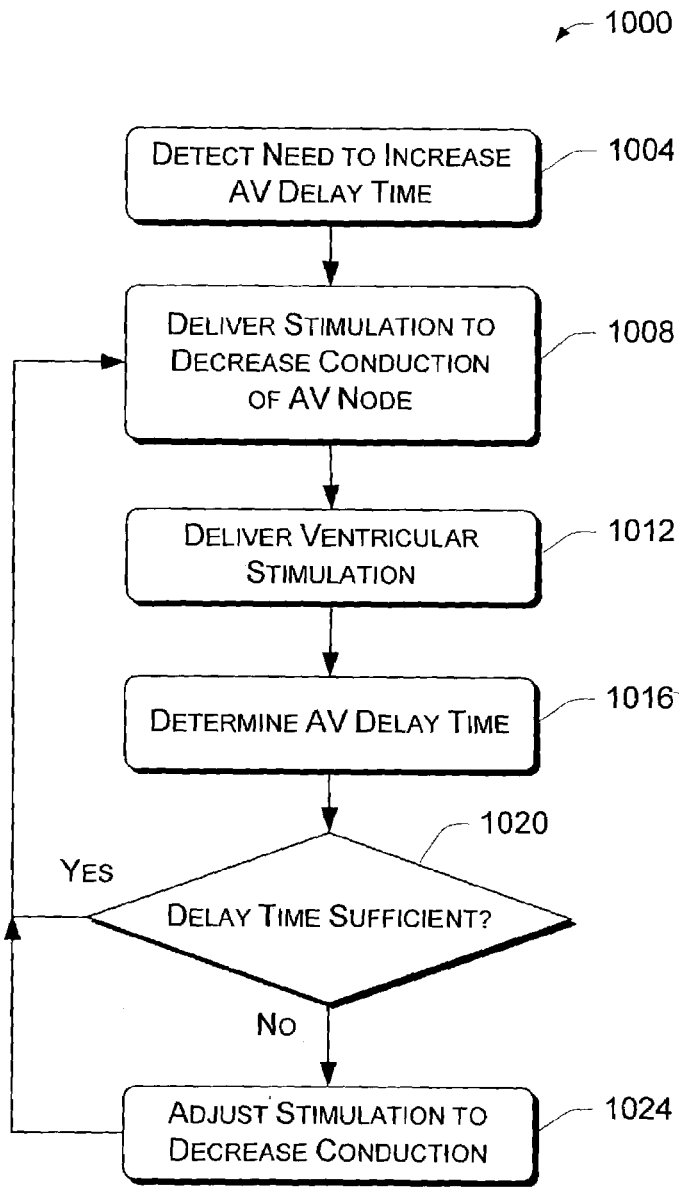
FIG. 10 is a block diagram of an exemplary method for stimulating a parasympathetic nerve to affect conduction of a patient's AV node wherein the method includes delivering ventricular stimulation.

FIG. 10 shows a block diagram of an exemplary method 1000 that includes stimulation to decrease AV nodal conduction and ventricular stimulation. In this example, the term AV node may include AV bundle. In a detection block 1004, a need to increase AV delay time is detected. The need may be based on physiologic and/or other factors. For example, an implanted device, a patient and/or a physician may aid in detecting a need to increase AV delay time. An implanted device may rely on one or more sensors and/or an algorithm to detect a need to increase AV delay time, a patient may experience symptoms associated with inadequate cardiac function that may benefit from an increase in AV delay time, and/or a physician may wish to make a diagnosis or to prescribe a therapy that relies on a certain minimum AV delay time. In this example, the need to increase AV delay time is optionally related to a therapy that includes ventricular stimulation, such as, a ventricular pacing therapy.

In another example, a need to increase AV delay time may arise from an atrial pacing therapy. For example, in antitachycardiac pacing, atrial overdrive pacing may be used to terminate a supraventricular arrhythmia (SVA). In this example, an increase in AV delay time or induction of some degree of block may act to filter atrial activity to reduce the effect of the high rate of atrial pacing and/or arrhythmia on the ventricles. Hence an exemplary method may include implementing an antitachycardia pacing therapy, for example, that relies on overdrive pacing, and stimulating a parasympathetic nerve associated with the atrio-ventricular node to achieve a desired ratio of transmitted activation wavefronts to atrial pacing pulses.

Referring again to the exemplary method 1000 of FIG. 10, a stimulation delivery block 1008 follows, wherein stimulation is delivered to decrease conduction of the AV node. In the exemplary method 1000, the stimulation may be directed to a parasympathetic nerve, another nerve and/or tissue. For example, stimulation of a parasympathetic nerve may cause a decrease in AV conduction as described above while stimulation of another nerve or tissue may cause the AV node to experience at least some refractoriness. A ventricular stimulation delivery block 1012 follows wherein one or more stimuli are delivered to one or both ventricles. Of course, the ventricular stimulation delivery block 1012 optionally occurs prior to and/or after the stimulation delivery block 1008. The ventricular stimulation delivery block 1012 optionally operates according to one or more pacing therapies that include ventricular pacing and/or stimulation. Such an exemplary method may include stimulating a parasympathetic nerve associated with the AV node to thereby slow conduction of the AV node; and, prior to passage of an activation wavefront through the AV node, delivering one or more stimuli to one or both of the ventricles. In this example, the delivering may include delivering a stimulus to the right ventricle and delivering a stimulus to the left ventricle at the same or at different times. Further, such an example may include delivering a stimulus to an atrium prior to the delivering a stimulus to one or both ventricles. Of course, a target AV delay time may depend on desired atrial and/or ventricular stimulation associated with a therapy.

A determination block 1016, which may occur during or after delivery of the stimulation of blocks 1008 and 1012, aims to determine the effect of the stimulation on AV delay time. Such a determination block may compensate for respiratory effects on AV delay time, for example, AV delay time may be measured over a number of cardiac cycles wherein the number covers both inspiration and expiration phases of a respiratory cycle (e.g., one, two, three or more respiratory cycles). The determination block 1016 may determine an average or other statistical delay time. In general, the determination block 1016 relies on detection of an atrial event and detection of a ventricular event; however, other techniques may be available to determine AV delay time.

According to the exemplary method 1000, responsive to the determining, a decision block 1020 decides whether the AV delay time is sufficient, for example, with respect to a desired increase and/or some minimum AV delay time. If the decision block 1020 decides that the delay time is sufficient, then the method 1000 continues in at the delivery block 1008 wherein the method optionally uses the same stimulation parameters to ensure proper timing of a subsequent cardiac cycle that includes ventricular stimulation. If the decision block 1020 decides that the delay time is not sufficient, then the exemplary method 1000 continues in an adjustment block 1024 that adjusts one or more stimulation parameters in an effort to achieve a more appropriate AV delay time. The method 1000 then continues at the delivery block 1008.

Another exemplary method includes stimulating a parasympathetic nerve associated with the atrio-ventricular node to thereby slow conduction of the atrio-ventricular node; and controlling ventricular contractions using a combination of atrial activation wavefronts passing through the atrio-ventricular node and stimulation pulses to one or both of the ventricles wherein each of the stimulation pulses occurs after an atrial activation and prior to passage of the atrial activation wavefront through the atrio-ventricular node. Such an exemplary method may act to reduce the number of stimulation pulses applied to one or both of a patient's ventricles. Such an exemplary method optionally implements a timing window wherein upon expiration of the timing window delivery of a stimulation pulse to a ventricle occurs. Such a window may commence upon detection of an atrial event (e.g., a paced event and/or an intrinsic event). Such an exemplary method optionally includes detecting a ventricular contraction (R wave) and initiating a ventricular to atrial interval wherein upon expiration of the interval, delivery of an atrial stimulus occurs.

While the foregoing exemplary methods 900, 1000 have been set forth as separate methods, combination of the various blocks within these methods is also possible. In addition, according to various exemplary methods (e.g., 900, 1000, etc.) and/or devices, stimulation occurs optionally at a non-epicardial location and/or at an epicardial location. For example, suitable non-epicardial locations include, but are not limited to, right and left cervical vagal locations. Of course, locations also optionally include those associated with afferent parasympathetic pathways.

Stimulation of Epicardial Nerves and/or Tissue Regions

Figure 11:
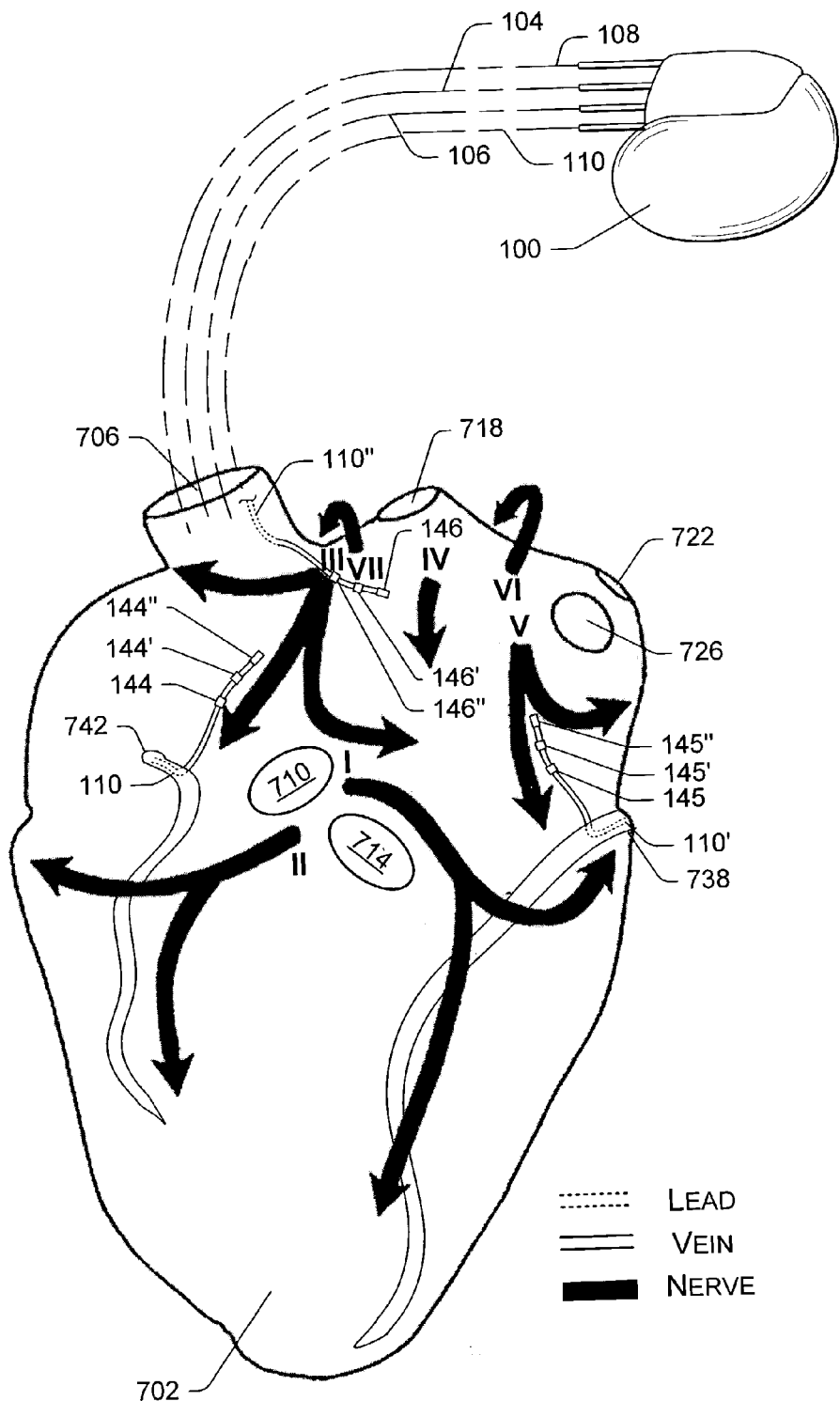
FIG. 11 is an approximate anatomical ventral view diagram of a human heart including some arteries, veins and nerves and stimulation leads associated with a pacing device.

Referring again to FIGS. 7 and 8, various epicardial vessels are shown along with various subplexuses. Referring to FIG. 11, an approximate anatomical diagram of a ventral view of a heart that corresponds to the diagram of FIG. 7 is shown. In FIG. 11, exemplary leads having exemplary electrodes are also shown in exemplary epicardial locations. For example, FIG. 11 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 11, one exemplary lead 110 has an electrode portion having three electrodes 144, 144', 144". The electrode portion of the lead 110 passes through the wall of the anterior cardiac vein 742 and extends along nerves emanating from the VRA (III) subplexus. Having an electrode portion of a lead positioned as such, activation of at least one of the electrodes 144, 144', 144" optionally stimulate nerves to release acetylcholine and/or affect operation of the SA node. In a similar manner, another exemplary lead 110' has an electrode portion having three electrodes 145, 145', 145". The electrode portion of the lead 110' passes through the wall of the great cardiac vein 738 and extends along nerves emanating from the LD (V) subplexus. Having an electrode portion of a lead positioned as such, activation of at least one of the electrodes 145, 145', 145" optionally stimulate nerves to release acetylcholine and/or affect operation of the AV node. Yet another exemplary lead 110" has an electrode portion having three electrodes 146, 146', 146". The electrode portion of the lead 110" passes through the wall of the superior vena cava (see, e.g., opening of superior vena cava labeled 706) and extends to the VRA (III) subplexus and/or DRA (VII) subplexus. Having an electrode portion of a lead positioned as such, activation of at least one of the electrodes 146, 146', 146" optionally stimulate nerves to release acetylcholine and/or affect operation of the SA node. Of course, the locations and functions of the three leads 110, 110', 110" are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference. While the leads shown in FIG. 11 include electrode portions that extend through a vessel and/or chamber wall, other exemplary leads include electrode portions that remain within the lumen of a vessel and/or within a chamber of the heart. Again, such leads optionally extend to pre-ganglionated field regions, ganglionated field regions and/or post-ganglionated field regions associated with at least one of the seven subplexus identified in the Pauza et al. reference. Further, exemplary leads optionally include electrode portions that remain within the lumen of a vessel and/or within a chamber of the heart.

Figure 12:
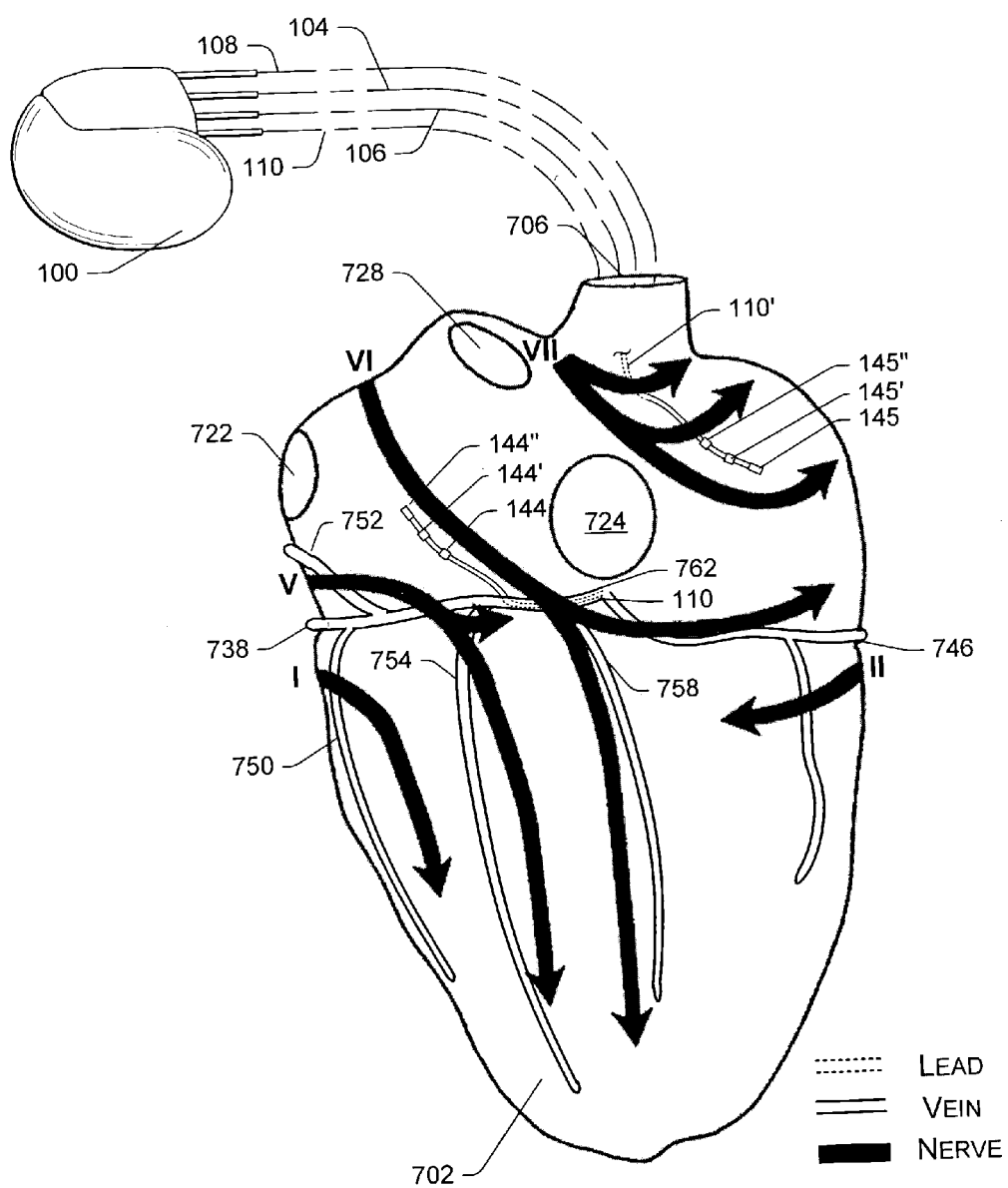
FIG. 12 is an approximate anatomical dorsal view diagram of a human heart including some arteries, veins and nerves and stimulation leads associated with a pacing device.

Referring to FIG. 12, an approximate anatomical diagram of a ventral view of a heart that corresponds to the diagram of FIG. 8 is shown. FIG. 12 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 12, one exemplary lead 110 has an electrode portion having three electrodes 144, 144', 144". The electrode portion of the lead 110 passes through the wall of the coronary sinus 662 and extends along nerves emanating from the MD (VI) subplexus and/or LD (V) subplexus. Having an electrode portion of a lead positioned as such, activation of at least one of the electrodes 144, 144', 144" may stimulate nerves to release acetylcholine and/or affect operation of the AV node. In a similar manner, another exemplary lead 110' has an electrode portion having three electrodes 145, 145', 145". The electrode portion of the lead 110' passes through the wall of the superior vena cava (see, e.g., opening of superior vena cava labeled 706) and extends to the DRA (VII) subplexus and/or to nerves emanating from the DRA (VII) subplexus. Having an electrode portion of a lead positioned as such, activation of at least one of the electrodes 145, 145', 145" may stimulate nerves to release acetylcholine and/or affect operation of the SA node. Of course, the locations and functions of the two leads 110, 110' are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference.

Figure 13:
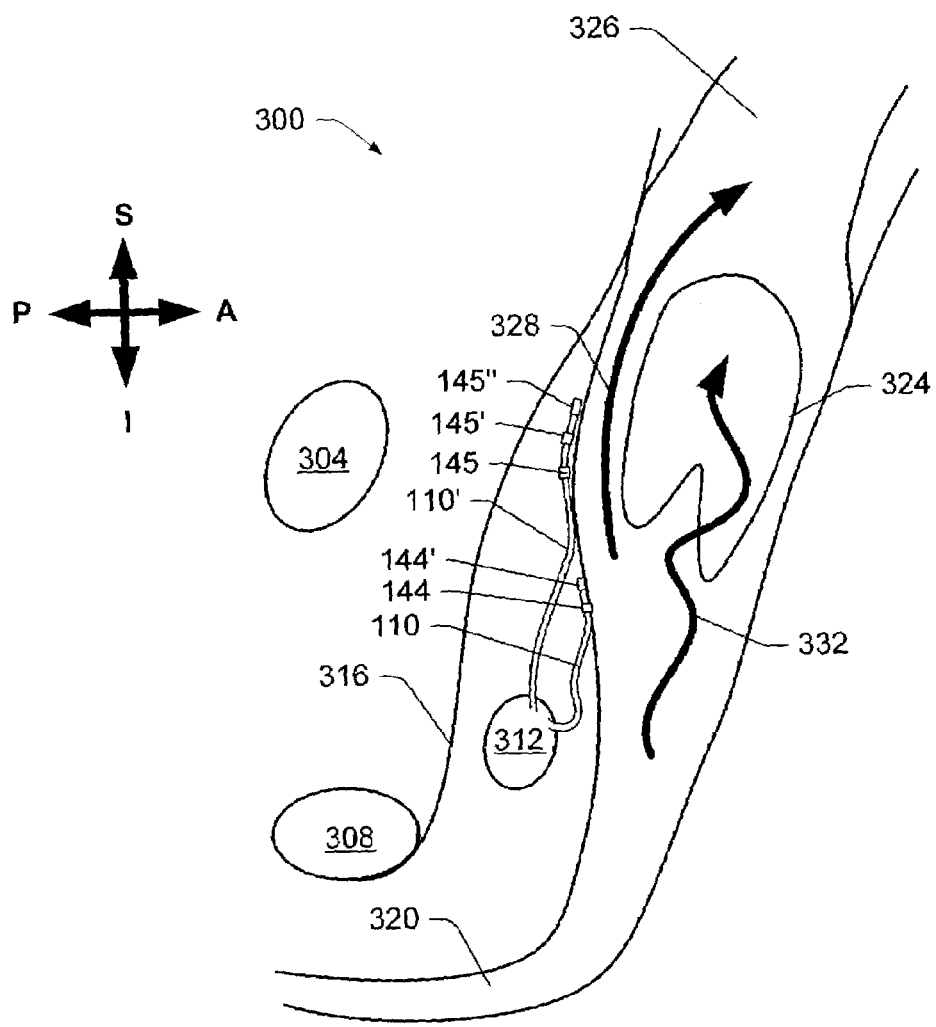
FIG. 13 is an approximate anatomical diagram of an AV nodal region including exemplary leads and/or electrode portions.

Referring to FIG. 13, the approximate anatomical diagram 300 of FIG. 3 is shown along with two electrode portions 110, 110'. In this exemplary method, the electrode portions 110, 110' access the right atrium via a patient's coronary sinus 312. One electrode portion 110 is positioned inferior to the approximate AV node 324 and the other electrode portion 110' is positioned approximately along the inferior-superior axis at approximately the same position as the AV node 324. Yet another electrode portion is optionally positioned superior to the AV node 324 along the AV bundle region 326. Of course, an exemplary method may include one or more electrode portions positioned inferior, equal and/or superior to the AV node 324. In general, an electrode portion is positioned posterior to the AV node 324; however, other positioning is within the scope of various exemplary methods.

The electrode portions 110, 110' have one or more corresponding electrodes. For example, the electrode portion 110 includes a ring electrode 144 and a distal tip electrode 144'. Similarly, the electrode portion 110' includes two ring electrodes 145, 145' and a distal tip electrode 145". The various electrodes and/or electrode portions are optionally secured via cauterization means, anchoring means, etc. For instance, cauterization means optionally includes heating at least part of the electrode portion to secure the electrode portion to tissue. Anchoring means optionally includes screws, biasing prong(s), hooks, etc.

According to the diagram of FIG. 13, a stimulation device is configured to deliver stimulation pulses to the electrode portions 110, 110'. Further, the stimulation device optionally determines whether to shunt or induce "fast" and/or "slow" pathway conduction. The stimulation device is optionally configured to affect operation and/or conduction of the AV node and/or AV bundle via exemplary electrode portions 110, 110'. Of course, a stimulation device optionally stimulates nerves and/or tissue at such locations and/or at other locations. In another example, an electrode is located epicardially and at a position wherein stimulation of the AV node and/or AV bundle is possible.

As already mentioned, an electrode may be positioned proximate to the AV node and/or AV bundle and used to deliver stimuli to decrease conduction in the AV node and to cause an evoked response of one or more chambers of the heart. Such an electrode may be used in a manner to cause an evoked response when target myocardium is not refractory and to decrease conduction in the AV node when the target myocardium is refractory. Of course, such an electrode may stimulate a parasympathetic nerve that acts to decrease AV nodal conduction as well. Various exemplary methods optionally use such an electrode to achieve a desired AV delay time and/or to stimulate a chamber of the heart. In various exemplary methods, one or more stimulation parameters are chosen to selectively stimulate AV nodal tissue to reduce conduction (e.g., refractoriness, tetanus, fatigue, etc.), a parasympathetic nerve to cause release of acetylcholine and/or to effectuate a brain response and/or myocardium in a manner sufficient to cause an evoked response. In general, tetanus is a state of continuous muscular contraction that may be induced via relatively rapid and repeated stimuli and fatigue is due to a lack of energy and/or a build up of waste products. Fatigue may be classified as twitch fatigue (e.g., due to a series of contractions that do not cause a state of tetanus) or tetanus fatigue (e.g., due to a state of tetanus).

While FIGS. 11, 12 and 13 show electrode portions and/or leads labeled "110", such electrode portions and/or leads optionally stem from the leads 104, 106, 108 of the stimulation device 100, as shown in FIG. 1.

According to various exemplary methods, delivery of one or more stimulation pulses affects conduction and/or operation of an AV node and/or AV bundle. Such exemplary methods optionally include detecting a need for altering conduction and/or operation of the AV node and/or the AV bundle. Such exemplary methods optionally include delivering a stimulation pulse to a first electrode portion having one or more electrodes positioned proximate to the AV node and/or AV bundle and/or delivering a stimulation pulse to a second electrode portion having one or more electrodes positioned proximate to a parasympathetic pathway. In such exemplary methods, delivery of a stimulation pulse to the first electrode portion optionally causes the AV node and/or AV bundle to enter a refractory period and/or delivery of a stimulation pulse to the second electrode portion causes a decrease in conduction through the AV node and/or AV bundle.

Yet another exemplary method includes delivering a stimulation pulse to one electrode portion having one or more electrodes positioned proximate to the AV node and/or AV bundle and proximate to a parasympathetic pathway to cause the AV node and/or AV bundle to enter a refractory period and to reduce conduction of the AV node and/or AV bundle. While yet another exemplary method includes delivering a stimulation pulse to a first electrode portion having one or more electrodes positioned inferior to the AV node and/or delivering a stimulation pulse to a second electrode portion having one or more electrodes positioned equal to and/or superior to the AV node; and delivering a stimulation pulse to a third electrode portion having one or more electrodes positioned proximate to a parasympathetic pathway to reduce conduction of the AV node and/or AV bundle. As explained below, delivering optionally occurs postinspiration.

Various exemplary methods optionally include positioning one or more electrodes in the superior vena cava (SVC), the inferior vena cava (IVC) and/or the coronary sinus (CS). Other sites may include jugular veins or other veins proximate to parasympathetic nerves or pressure sensors that can trigger parasympathetic responses. Various exemplary methods optionally include positioning one or more electrodes in the azygous vein. Suitable electrode portions for positioning electrodes in or near a nerve and/or the heart include, but are not limited to, basket type or double helix type of electrode portions, see, e.g., U.S. patent application having Ser. No. 10/321,307, filed Dec. 16, 2002, entitled "Implantable lead and electrode portion", to Helland and Shelchuk, which is incorporated by referenced herein, and U.S. patent application having Ser. No. 10/000,333, filed Oct. 22, 2001, entitled "Implantable lead and method for stimulation the vagus nerve", to Weinberg, which is incorporated by reference herein.

In various exemplary methods, stimulation to affectAV conduction aims to avoid producing an evoked response from the myocardium (e.g., contraction of a chamber). In this regard, such stimulation may occur according to a power, frequency, duty cycle, phase (e.g., monophasic, biphasic, triphasic, etc.) that reduces the risk of myocardial stimulation and/or the stimulation may occur during a refractory period of the myocardium to reduce the risk of myocardial stimulation.

Determining Vagal Tone and/or Inspiration/Postinspiration

Figure 14:
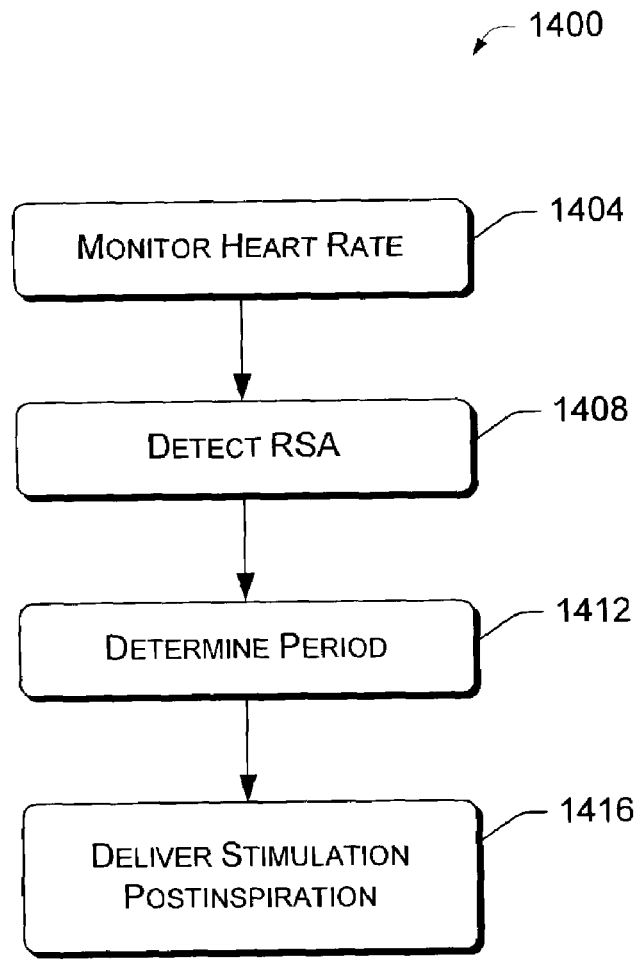
FIG. 14 is a block diagram of an exemplary method for delivering a stimulation pulse postinspiration.

As already mentioned, Mendelowitz noted that "cardiac vagal neurons recorded in vivo receive inhibitory synaptic input during inspiration, which is then followed by a rapid depolarization caused by excitatory synaptic input during postinspiration". Therefore, for a variety of reasons, the aforementioned exemplary methods and/or device optionally stimulate nerves and/or tissue postinspiration, i.e., not during inspiration. Referring to FIG. 14, an exemplary method 1400 for delivery of one or more stimulation pulses postinspiration is shown. In a monitoring block 1404, a stimulation and/or other device monitors directly and/or indirectly heart rate. Next, in a detection block 1408, the stimulation and/or other device detects respiratory sinus arrhythmia. Following detection, in a determination block 1412, the stimulation and/or other device determines a period associated with inspiration. Next, in a delivery block 1416, the stimulation device delivers a stimulation pulse to a nerve and/or tissue region. Also note that such a method can determine a patient's vagal tone.

In another exemplary method, a stimulation and/or other device monitors inspiration directly and/or indirectly through use of a ventilation module and/or sensor. In this exemplary method and the aforementioned method, stimulation pulse delivery during postinspiration only can decrease power demand on an implantable stimulation device. In yet another exemplary method, parasympathetic stimulation pulse delivery occurs during a refractory period to avoid stimulation of cardiac and/or other tissue. Of course, an exemplary combined method optionally includes delivery of a stimulation pulse postinspiration in a refractory period.

Stimulation Postinspiration and/or Synchronous with Heart

Figure 15:
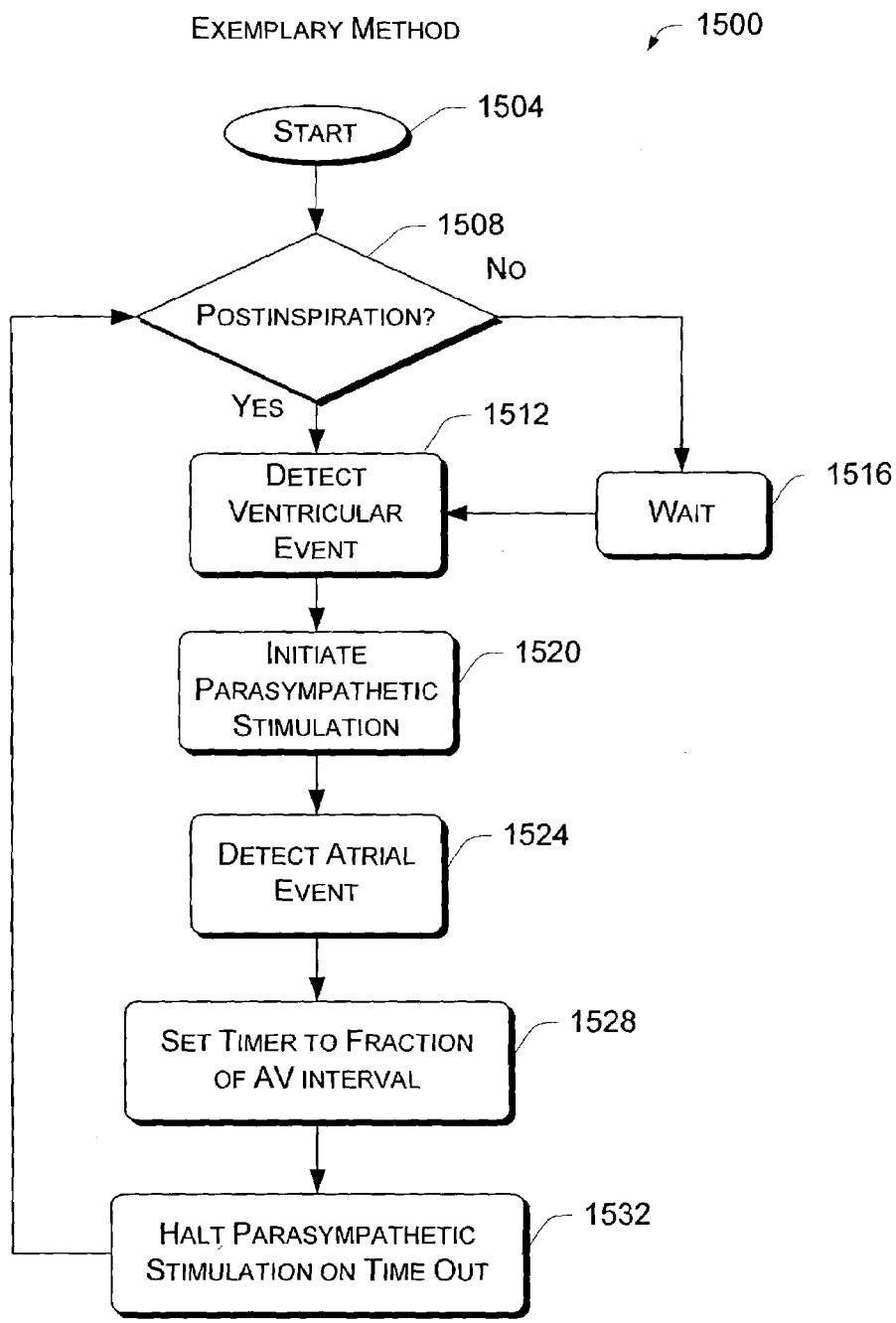
FIG. 15 is a block diagram of an exemplary method for delivering parasympathetic stimulation during a postinspiration phase and/or based on detection of one or more cardiac events.

As already mentioned, stimulation to slow AV conduction (e.g., parasympathetic and/or other stimulation) may occur postinspiration (e.g., not during inspiration) and/or in synchrony with one or more cardiac events (e.g., events typically found in a cardiac cycle). FIG. 15 shows an exemplary method 1500 wherein parasympathetic stimulation occurs according to respiratory cycle and/or according to one or more events in a cardiac cycle. Various exemplary methods presented herein may implement one or more of the blocks or procedures described with reference to the exemplary method 1500.

A start block 1504 may occur at anytime an exemplary method desires to implement parasympathetic nerve stimulation. A decision block 1508 follows that determines whether a patient is in a postinspiration phase of a respiratory cycle. For example, an exemplary device may detect impedance, movement of an implanted device, pressure, cardiac characteristics, autonomic tone, etc., and then use such information to determine one or more phases of a respiratory cycle. In the exemplary method 1500, if the decision block 1508 determines that a patient is not in a postinspiration phase, then the method 1500 may continue in a wait block 1516, which either causes an appropriate delay or waits for an event indicative of a postinspiration phase. If the decision block 1508 determines that a patient is in a postinspiration phase, the method 1500 continues in a ventricular event detection block 1512; the wait block 1516 also continues at the ventricular event detection block 1512. In general, the ventricular event detection block 1512 aims to detect an R wave or a ventricular contraction. As described above, parasympathetic stimulation may act to decrease AV conduction and hence increase AV delay time.

Upon detection of a particular event, the method 1500 then initiates parasympathetic stimulation in an initiation block 1520. The stimulation may continue for a set period of time, may continue until detection of another cardiac event or may continue for a certain amount of time based on detection of a subsequent cardiac event. As shown in FIG. 15, the method 1500 includes an atrial event detection block 1524. For example, such a detection block may detect an atrial paced event and/or an intrinsic atrial event. Upon detection of the atrial event, the method 1500 proceeds to set a timer to a fraction of an atrio-ventricular interval or other suitable interval in a set timer block 1528. Upon expiration of the timer, a halt parasympathetic stimulation block 1532 halts parasympathetic stimulation. In this example, parasympathetic stimulation may be halted to ensure that the parasympathetic stimulation does not cause any significant detriment to active contractility. Thereafter, the exemplary method 1500 continues at the decision block 1508, at the detection block 1512 or at another suitable point (e.g., a decision block that decides whether further parasympathetic stimulation is required). Of course, as mentioned above, parasympathetic stimulation may be delivered during a refractory period of the myocardium or a portion thereof that may participate significantly in contraction of a chamber of the heart. Hence, the exemplary method 1500 optionally includes stimulating during a refractory period, for example, to reduce the risk of producing an evoked response from the myocardium.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein parasympathetic tuning via parasympathetic nerve stimulation aims to decrease heart rate and/or decrease AV conduction. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory decrease in heart rate (e.g., an increase of therapeutic value) and/or decrease in AV conduction. In this exemplary method, for example, a physician may slowly move a lead throughout an appropriate region and deliver pulses until a desired decrease in heart rate and/or AV conduction is seen maximally via monitoring.

In yet another exemplary method, a lead and/or an electrode are optionally positioned to increase parasympathetic activity while at the same time minimizing stimulation effects on heart rate. Once a "sweet spot" is found, then pulse parameters are optionally adjusted to minimize electrical power consumption, for example, by previously mentioned exemplary methods.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method comprising:
    implementing an antitachycardia pacing therapy that relies on atrial overdrive pacing using an electrode positioned on or in an atria and near the atrio-ventricular node;
    during a refractory period of the atrial overdrive pacing stimulating a parasympathetic nerve at the atrio-ventricular node in order to block all activation wavefronts from stimulating one or both ventricles using the same electrode used for atrial overdrive pacing; and
    subsequent to the parasympathetic nerve stimulation, implementing ventricular pacing.

2. The method of claim 1 further comprising providing the electrode on a lead adapted for placing the electrode along nerves emanating from one of the LD(V) subplexus and the MD(VI) subplexus.

3. The method of claim 2 wherein the lead is further adapted for passing through the wall of a vessel and placing the electrode on an epicardial surface of the heart.

4. A method comprising:
    implementing an antitachycardia pacing therapy that relies on atrial overdrive pacing using an electrode positioned on or in an atria and near the atrio-ventricular node;

selecting a stimulation parameter which includes at least one of power, frequency, duty cycle, and phase, that blocks all atrial activation wavefronts from stimulating one or both ventricles;

using the selected stimulation parameter, stimulating a parasympathetic nerve at the atrio-ventricular node using the same electrode used for the atrial overdrive pacing; and subsequent to the nerve stimulation, implementing ventricular pacing.

5. The method of claim 4 further comprising providing the electrode on a lead adapted for placing the electrode along nerves emanating from one of the LD(V) subplexus and the MD(VI) subplexus.

6. The method of claim 5 wherein the lead is further adapted for passing through the wall of a vessel and placing the electrode on an epicardial surface of the heart.

* * * * *